| (12) | United States Patent | (10) Patent No.: | US 10,902,526 B2 |
|---|---|---|---|
| | Mercs | (45) Date of Patent: | Jan. 26, 2021 |

(54) SYSTEMS AND METHODS OF GENERATING CONSCIOUSNESS AFFECTS

(71) Applicants: Twiin, LLC, San Luis Obispo, CA (US); James Mercs, Huntington Beach, CA (US)

(72) Inventor: James Mercs, Huntington Beach, CA (US)

(73) Assignee: TWIIN, LLC, San Luis Obispo, CA (US)

( * ) Notice: Subject to any disclaimer, the term of this patent is extended or adjusted under 35 U.S.C. 154(b) by 263 days.

(21) Appl. No.: 15/561,981

(22) PCT Filed: Mar. 30, 2016

(86) PCT No.: PCT/US2016/024943
§ 371 (c)(1),
(2) Date: Sep. 27, 2017

(87) PCT Pub. No.: WO2016/160941
PCT Pub. Date: Oct. 6, 2016

(65) Prior Publication Data
US 2019/0108597 A1    Apr. 11, 2019

Related U.S. Application Data

(60) Provisional application No. 62/165,190, filed on May 21, 2015, provisional application No. 62/140,432, filed on Mar. 30, 2015.

(51) Int. Cl.
*G06Q 50/00*      (2012.01)
*H04L 12/58*      (2006.01)
(Continued)

(52) U.S. Cl.
CPC ............. *G06Q 50/01* (2013.01); *A61B 5/165* (2013.01); *H04L 29/08* (2013.01); *H04L 51/32* (2013.01);
(Continued)

(58) Field of Classification Search
None
See application file for complete search history.

(56) References Cited

U.S. PATENT DOCUMENTS 7,640,304 B1    12/2009  Goldscheider
8,478,582 B2    7/2013   Habu et al.
(Continued)

FOREIGN PATENT DOCUMENTS

CN          101370195 A     2/2009
KR    10-2013-0110965 A     10/2013
(Continued)

OTHER PUBLICATIONS

Comeau, Lisa Marie. "Knowing Better": Toward a Genealogy of Critical Consciousness. Order No. NR05972 The University of Regina (Canada), 2005 Ann ArborProQuest. Aug. 29, 2019 . (Year: 2005).*
(Continued)

*Primary Examiner* — Andrew B Whitaker
(74) *Attorney, Agent, or Firm* — EcoTech Law Group, P.C.

(57) ABSTRACT

A method of generating a consciousness affect is described. The method includes: (i) receiving, from a client device, a first and a second consciousness inputs, wherein the client device is associated with one or more users and the two consciousness inputs are different from each other; (ii) calculating a consciousness affect for one or more of the users; (iii) storing, in memory of the server and/or the client device, the consciousness affect; and (iv) wherein the first
(Continued)

consciousness input includes at least one input chosen from a group comprising emotional state input, reasoned input, location information input, physical awareness input and spiritual insight input, and the second consciousness input is at least one input chosen from a group comprising reasoned input, location information input, physical awareness input and spiritual insight input.

13 Claims, 24 Drawing Sheets

(51) Int. Cl.
*H04L 29/08* (2006.01)
*H04W 4/029* (2018.01)
*A61B 5/16* (2006.01)

(52) U.S. Cl.
CPC .............. *H04L 67/18* (2013.01); *H04L 67/22* (2013.01); *H04W 4/029* (2018.02)

(56) References Cited

U.S. PATENT DOCUMENTS

| | | |
|---|---|---|
| 8,825,515 B1 | 9/2014 | Hanson |
| 8,930,819 B1 | 1/2015 | Chan et al. |
| 9,129,008 B1 | 9/2015 | Kuznetsov |
| 9,134,215 B1 | 9/2015 | Vignisson et al. |
| 2008/0313108 A1* | 12/2008 | Carrabis ............... A61B 5/165 706/11 |
| 2011/0179003 A1 | 7/2011 | Min et al. |
| 2012/0101966 A1* | 4/2012 | van Coppenolle ..... H04L 63/10 706/20 |
| 2012/0179751 A1 | 7/2012 | Ahn et al. |
| 2013/0019187 A1 | 1/2013 | Hind et al. |
| 2013/0144937 A1* | 6/2013 | Lee ....................... G06Q 50/01 709/203 |
| 2013/0204664 A1 | 8/2013 | Romagnolo et al. |
| 2013/0216989 A1* | 8/2013 | Cuthbert ............... A61B 5/721 434/238 |
| 2013/0247078 A1 | 9/2013 | Nikankin et al. |
| 2013/0325870 A1* | 12/2013 | Rouse .................. G06F 16/353 707/741 |
| 2014/0004489 A1 | 1/2014 | Kim et al. |
| 2014/0032277 A1* | 1/2014 | Kashyap .......... G06Q 10/06393 705/7.39 |
| 2014/0136450 A1* | 5/2014 | Lee ........................ G06N 7/005 706/11 |
| 2014/0181744 A1* | 6/2014 | Rivers, Jr. ........... G06F 3/04817 715/826 |
| 2014/0207797 A1 | 7/2014 | Davies |
| 2014/0223329 A1 | 8/2014 | Falaki et al. |
| 2014/0223462 A1* | 8/2014 | Aimone ................ G16H 40/67 725/10 |
| 2014/0282651 A1 | 9/2014 | Baratz |
| 2014/0298364 A1 | 10/2014 | Stepanov et al. |
| 2014/0323817 A1* | 10/2014 | el Kaliouby ........... G16H 20/70 600/300 |
| 2014/0347265 A1* | 11/2014 | Aimone ................ A61M 21/00 345/156 |
| 2014/0365208 A1* | 12/2014 | De Choudhury ...... G06Q 50/01 704/9 |
| 2015/0058416 A1 | 2/2015 | Felt |
| 2015/0061825 A1* | 3/2015 | Suzuki ................... H04W 4/21 340/5.52 |
| 2015/0121251 A1* | 4/2015 | Kadirvel ............... G06F 3/0484 715/753 |
| 2015/0227208 A1 | 8/2015 | Blevins et al. |
| 2015/0319119 A1 | 11/2015 | Ryu et al. |

FOREIGN PATENT DOCUMENTS

| | | |
|---|---|---|
| WO | 2014/138781 A1 | 9/2014 |
| WO | 2014191996 A1 | 12/2014 |

OTHER PUBLICATIONS

International Search Report and Written Opinion received for PCT Application No. PCT/US2016/024943 dated Jul. 1, 2016, 14 pages.
Commuincation pursunat to Rule 164(1) EPC received for EP Application No. 16774079.4 dated Oct. 2, 2018, 17 pages.
Wakade et al., "Text Mining for Sentiment Analysis of Twitter Data", 2012, 6 Pages.
Jamoussi et al., "Dynamic construction of dictionaries for sentiment classification", Cloud and Green Computing (CGC), Third International Conference on 2013 dated Sep. 30-Oct. 2, 2013, 2 Pages.
Azmina et al., "Sentiment Analysis: Determining People's Emotions in Facebook", 2014, 6 Pages.
Sanchez et al., "Sentiment Analysis for e-Services", 2014, 2 Pages.
Extended European Search Report for EP Application No: 16774079.4 dated Jan. 16, 2019, 15 pages.

* cited by examiner

Location Information Input

| Category | More | Default | Less | Rank |
|---|---|---|---|---|
| Attraction | 14 | 16 | 18 | 1 |
| Replusion | 12 | 14 | 16 | 2 |
| Calm | 10 | 12 | 14 | 3 |
| Unrest | 8 | 10 | 12 | 4 |
| Anticipate | 6 | 8 | 10 | 5 |
| Remember | 4 | 6 | 8 | 6 |
| Soitude | 2 | 4 | 6 | 7 |
| Congestion | 1 | 2 | 4 | 8 |

FIG. 6D

Reasoned Input

| Category | More | Default | Less | Rank |
|---|---|---|---|---|
| Understood | 12 | 14 | 16 | 1 |
| Solve | 10 | 12 | 14 | 2 |
| Recognize | 8 | 10 | 12 | 3 |
| Sight | 6 | 8 | 10 | 4 |
| Hear | 4 | 6 | 8 | 5 |
| Smell | 2 | 4 | 6 | 6 |
| Touch | 2 | 3 | 4 | 7 |
| Taste | 1 | 2 | 3 | 8 |

FIG. 6E

| 702 | Retrieving or receiving, from memory of a client device and/or a server, one or more shares, each of which contains one or more submissions | val shares = Storage.findSharesByGroupId(id) |
|---|---|---|
| 704 | Identifying, in each of the submissions, information relating to one or more consciousness input types | Use, for example, a speech-to-consciousness state module and/or a facial recognition module |
| 706 | Extracting, from one or more of the consciousness input types, information relating to one or more consciousness input categories ("categories") | val consiciousEmotions = getConsciousEmotionsValues(shares)<br>/* List(("Love", "more", 32, "0 hours", 1.0),<br>val consiciousSpiritual = getConsciousSpiritualValues(shares)<br>/* List(("Hug", "self", 18, "0 hours", 1.0),<br>    ("Hug", "self", 18, "75 days", 0.5),<br>    ("Hug", "self", 18, "8 month", 0)) */<br><br>val consiciousLocation = getConsciousLocationValues(shares)<br>/* List(("Remember", "less", 4, "0 hours", 1.0),<br>    ("Remember", "less", 4, "32 days", 0.75),<br>    ("Remember", "less", 4, "7 month", 0)) */<br><br>val consiciousPhysical = getConsciousPhysicalValues(shares)<br>/* List(("Full", "more", 14, "0 hours", 1.0),<br>    ("Full", "more", 14, "75 days", 0.5),<br>    ("Full", "more", 14, "2 years", 0)) */<br><br>val consiciousReasoned = getConsciousReasonedValues(shares)<br>/* List(("Recognize", "totally", 12, "0 hours", 1.0),<br>    ("Recognize", "totally", 12, "75 days", 0.5),<br>    ("Recognize", "totally", 12, "1 year", 0)) */ |

FIG. 7

| | | |
|---|---|---|
| 708 | (Optional) Concatenating the information relating to one or more of the categories to form an electronic concatenated list of categories | val allConsciousValues = consiciousEmotions ++ consiciousSpiritual ++ consiciousLocation ++ consiciousPhysical ++ consiciousNeocortex<br>/* List(("Love", "more", 32, "0 hours", 1.0),<br>("Love", "less", 28, "32 days", 0.75),<br>("Love", "less", 28, "1 year", 0),<br>("Hug", "self", 18, "0 hours", 1.0),<br>("Hug", "self", 18, "75 days", 0.5),<br>("Hug", "self", 18, "8 month", 0),<br>("Remember", "less", 4, "0 hours", 1.0),<br>("Remember", "less", 4, "32 days", 0.75),<br>("Remember", "less", 4, "7 month", 0),<br>("Full", "more", 14, "0 hours", 1.0),<br>("Full", "more", 14, "75 days", 0.5),<br>("Full", "more", 14, "2 years", 0),<br>("Recognize", "totally", 12, "0 hours", 1.0),<br>("Recognize", "totally", 12, "75 days", 0.5),<br>("Recognize", "totally", 12, "1 year", 0)) */ |
| 710 | (Optional) Filtering the concatenated list to filter out information relating to certain undesired categories and form an electronic list of desired information relating to one or more of the categories | val filtered = allConsciousValues.filterBy(e => e.ageInMonths < 6)<br>/* List(("Love", "more", 32, "0 hours", 1.0),<br>("Love", "less", 28, "32 days", 0.75),<br>("Hug", "self", 18, "0 hours", 1.0),<br>("Hug", "self", 18, "75 days", 0.5),<br>("Remember", "less", 4, "0 hours", 1.0),<br>("Remember", "less", 4, "32 days", 0.75),<br>("Full", "more", 14, "0 hours", 1.0),<br>("Full", "more", 14, "75 days", 0.5),<br>("Recognize", "totally", 12, "0 hours", 1.0),<br>("Recognize", "totally", 12, "75 days", 0.5)) */ |

FIG. 7
(Continued)

| | | |
|---|---|---|
| 712 | (Optional) Grouping information relating to one or more of the desired categories to form one or more grouped lists, each of which contains desired information regarding a single category that is found in the filtered list. | val grouped = filtered.groupBy(e => (e.name, e.contribution)).mapValues(e => (e.name, e.contribution, e.percent))<br>/* List("Love" -> List((32, 1.0), (28, 0.75)),<br>"Hug" -> List((18, 1.0), (18, 0.5)),<br>"Remember" -> List((4, 1), (4, 0.75)),<br>"Full" -> List((14, 1.0),(0.5)),<br>"Recognize" -> List((12, 1.0), (12, 0.5))) */ |
| 714 | Computing a total contribution value for each of the grouped lists to arrive at a contribution list that shows one or more of the total contribution values for each category | val contributions = calculateContributions(grouped)<br>/* List("Love", -> (32 * 1.0 + 28 * 0.75),<br>"Hug" -> (18 * 1.0 + 18 * 0.5),<br>"Remember", -> (4 * 1.0 + 4 * 0.75),<br>"Full", -> (14 * 1.0 + 14 * 0.5),<br>"Recognize" -> (12 * 1.0 + 12 * 0.5)) */ |
| 716 | Generating, based on one or more of the total contribution values, a consciousness affect for one or more shares and that resolves the different total contribution values | val sorted - contributions.sortBy(c=> c.value)<br>/* List("Love" -> 53,<br>"Hug" -> 27,<br>"Full", -> 21,<br>"Recognize" -> 18,<br>"Remember" -> 6) */ |

FIG. 7
(Continued)

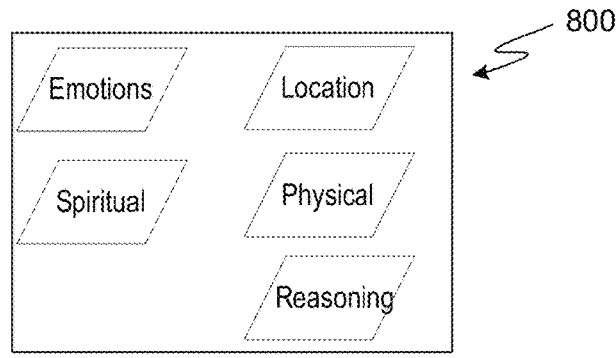

FIG. 8A

| 812 | 814 | 816 | 818 |
|---|---|---|---|
| Love more | 32 | 0 hours | 100% |
| Remember less | 4 | 7 month | 0% |
| Full more | 14 | 2 years | 0% |
| Recognize totally | 12 | 1 year | 0% |
| Hug self | 18 | 8 month | 0% |
| Love less | 28 | 32 days | 75% |
| Remember less | 4 | 32 days | 75% |
| Full more | 14 | 75 days | 50% |
| Recognize totally | 12 | 75 days | 50% |
| Hug self | 18 | 75 days | 50% |
| Love less | 28 | 1 year | 0% |
| Remember less | 4 | 0 hours | 100% |
| Full more | 14 | 0 hours | 100% |
| Recognize totally | 12 | 0 hours | 100% |
| Hug self | 18 | 0 hours | 100% |

FIG. 8B

| 812 | 814 | 816 | 818 |
|---|---|---|---|
| Love more | 32 | 0 hours | 100% |
| Remember less | 4 | 32 days | 75% |
| Full more | 14 | 75 days | 50% |
| Recognize totally | 12 | 75 days | 50% |
| Hug self | 18 | 75 days | 50% |
| Love less | 28 | 32 days | 75% |
| Remember less | 4 | 0 hours | 100% |
| Full more | 14 | 0 hours | 100% |
| Recognize totally | 12 | 0 hours | 100% |
| Hug self | 18 | 0 hours | 100% |

FIG. 8C

| Pitch Value | Display Color |
|---|---|
| 1-10 | Red |
| 11-20 | Orange |
| 21-30 | Yellow |
| 31-40 | Green |
| 41-50 | Blue |
| 51-60 | Indigo |
| 61-70 | Violet |

SYSTEMS AND METHODS OF GENERATING CONSCIOUSNESS AFFECTS

RELATED APPLICATION

The application claims priority from U.S. Provisional Applications having Ser. No. 62/140,432, filed on Mar. 30, 2015, and Ser. No. 62/165,910, filed on May 21, 2015, both of which are incorporated herein by reference for all purposes.

FIELD OF THE INVENTION

The present teachings generally relate to transforming consciousness inputs of one or more users into a visual and/or an audible representation of a consciousness affect. More particularly, the present teachings relate to network-based systems and methods that transform different consciousness inputs from one or more client devices, each of which is associated with one or more users, into a consciousness affect that is visually and/or audibly representable on one or more of the client devices.

BACKGROUND OF THE INVENTION

There are many systems and methods for people to communicate with other people over the Internet. Thus, for example, it is common for people to communicate by sending text or media between smartphones or computers. This communication can be between individuals or can be in a more public forum, where communication is with a group of people. There exist various social media websites where users may post updates on their page to their "status," which are then viewable by a select number of other users. Certain users may then elect to note that they "like" the status, comment on the status, or share the status with certain other users.

There is a need in the art for a method and apparatus that permits users to communicate more than whether they "like" or their emotional response to a post.

SUMMARY OF THE INVENTION

To this end, the present arrangements and teachings provide network-based systems and methods that resolve different inputs by the same or different users into an affect—referred herein to as a "consciousness affect."

According to the present teachings, in simple terms, consciousness affect is a calculated current state of awareness reached by a human at any given moment in time based on available mental and physical sensory inputs. Whether consciousness affect is shared or not, humans navigate through the physical world by calculating consciousness affects and acting or not acting on them. The present teachings define "consciousness" as a state of awareness of one's surroundings, or, of being aware of an external object or event, or awareness by the mind of itself and the world. Affect is defined as influence, act on, work on, have an impact on an outcome.

The present teachings believe that by making this calculated consciousness affect available (e.g., visually and/or audibly) to users in a social network, it is possible an any given point in time for anyone to see with great accuracy the current social cues on thoughts, desired actions, and feelings delineated by topic, product or event. Additionally, individuals are able to understand how their thoughts, actions, and feelings affect other individuals and groups, and vice versa.

The present teachings recognize that this understanding also allows for users to define groups based on user-programmable attributes, such as people, locations, topics, or any combination thereof and have the consciousness affect calculated in real-time for them.

In one aspect, the present arrangements provide a method of generating a consciousness affect. The method comprises: (i) receiving, from a client device, a first consciousness input and a second consciousness input, wherein the client device is associated with one or more users and the first consciousness input is different from the second consciousness input; (ii) calculating, using a server and/or the client device and based on the first consciousness input and the second consciousness input, a consciousness affect for one or more of the users; and (iii) storing, in memory of the server and/or the client device, the consciousness affect. The first consciousness input includes at least one input chosen from a group comprising emotional state input, reasoned input, location information input, physical awareness input and spiritual insight input, and the second consciousness input is at least one input chosen from a group comprising reasoned input, location information input, physical awareness input and spiritual insight input. Preferably, the calculating step is carried out in real-time, which is contemporaneous with the receiving step. In one embodiment of the present teachings, the method of generating a consciousness affect does not include the storing step, and after the calculating step proceeds to a step of visually and/or audible representing, on the client device, the consciousness affect.

In one embodiment of the present teachings, the method of generating a consciousness affect further comprises conveying the consciousness affect from the server to the client device. In one aspect of the present arrangements, the consciousness affect is represented on the client device. By way of example, representing the consciousness affect may include visually and/or audibly representing one representation chosen from a group comprising color, weather pattern, image, animation and sound.

In another embodiment of the present teachings, the method of generating a consciousness affect further comprises visually and/or the audibly representing a new consciousness affect over time when one or more new consciousness inputs of one or more users is received. One or more of the new consciousness inputs are received after (i.e., later in time than) the first consciousness input and the second consciousness input. In the above-mentioned step of receiving, the first and the second consciousness inputs are unprompted wherein one or more users are not providing the first and the second consciousness inputs in response to a server prompt and/or another user's input.

In one implementation of the present teachings, the first consciousness input and the second consciousness input are of a same type and the first consciousness input and the second consciousness input are one input chosen from a group comprising reasoned input, physical awareness input, location information input and spiritual insight input. However, in another embodiment of the present teachings, the first consciousness input and the second consciousness input are of different types, e.g., the first consciousness input is an emotional state and the second consciousness state input is at least one of a reasoned input, a physical awareness input, a location information input or a spiritual insight input.

The emotional state input represents an emotional state of the user. The reasoned input represents an expression of the user. The location information input represents location of the client devices. The physical awareness input includes one information, associated with the user and, chosen from a group comprising general health information, body type and biology awareness. The spiritual insight input represents an extra sense of presence or purpose associated one or more of the users.

In certain embodiments of the present teachings, other information is received in additional to the first consciousness input and the second consciousness input. By way of example, a user relies on location information associated with one or more of the client devices and provides a location information input. Thus, calculating the consciousness affect for one or more users, in one embodiment of the present teachings, accounts for this location information input by the user. In this example, the user obtains the location information from one source that is chosen from a group comprising satellite, global positioning system ("GPS"), 802.11 ("WiFi"), sensor, and radio frequency.

In another embodiment of the present teachings, the method of generating a consciousness affect further comprises: (i) computing, using the server and/or the client device, different consciousness affects at different instances in time for a particular location information; and (ii) representing, on the client device and for the particular location information, the different computed consciousness affects. Another step may include establishing, for one or more users, a baseline consciousness affect at the particular location. Yet another step may include identifying, for a particular time in a duration, the baseline consciousness at the particular location, and wherein the duration includes one member chosen from a group comprising minute, hour, day, week, month, year, decade and century.

In preferred embodiments of the present teachings, the user's emotional state input includes one category chosen from a group comprising love, no love, joy, sad, concerned, annoyed, trust, defiant, peaceful, aggressive, accept, reject, interested, distracted, optimistic and doubtful. The emotional state input is not the same as reasoned input, physical awareness input, location information input and spiritual insight input.

Similarly, the user's reasoned input preferably includes one category chosen from a group comprising understood, solve, recognize, sight, hear, smell, touch and taste. The reasoned input is not the same as emotional state input, physical awareness input, location information input and spiritual insight input.

When the user wishes to express his physical awareness, he may select from one category chosen from a group comprising fit, not fit, energetic, tired, healthy, sick, hungry and full. The physical awareness is not the same as emotional state input, reasoned input, location information input and spiritual insight input.

In connection with the location information, the user input may include one category chosen from a group comprising attraction, repulsion, calm, unrest, anticipate, remember, solitude and congestion. The location information input is not the same as emotional state input, reasoned input, physical awareness input, spiritual insight input.

The user's spiritual insight input is obtained when she/he selects one category chosen from a group comprising hug, missing, energy, shield, flash, deja vu, presence and universe. The spiritual insight input is not the same as emotional state input, reasoned input, physical awareness input and location information input.

In addition to receiving the first consciousness input and the second consciousness input, a first intensity information associated with the first consciousness input and a second intensity information associated with the second consciousness input may also be received or assigned. In absence of receiving the first intensity information and/or the second intensity information, the first intensity information may be assigned a first default intensity value and/or the second intensity information may be assigned a second default intensity value, respectively.

In one preferred embodiment of the present teachings, calculating a consciousness affect for one or more users further comprises: (i) identifying, in the first consciousness input and the second consciousness input, information relating to one or more consciousness input types; (ii) extracting, from the information relating to one or more of the consciousness input types, information relating to one or more categories of each of the consciousness input types ("categories") to generate a list identifying one or more extracted categories from each of the first consciousness input and the second consciousness input, and wherein each of the extracted categories is assigned a predetermined value that is at least in part based on the first intensity information or based on the second intensity information; (iii) assigning, based on an age of the first consciousness input, a first contribution value to the first consciousness input and assigning, based on an age of the second consciousness input, a second contribution value to the second consciousness input; (iv) determining, for each of the first consciousness input and the second consciousness input, a category contribution value, which represents a contribution of the first consciousness input and the first intensity information, or contribution of the second consciousness input and the second intensity information, to each the extracted category present in the list, and wherein the category contribution value equals a product of the predetermined value assigned to each of the extracted categories and the first contribution value or the second contribution value; (v) adding each category contribution value to arrive at a total contribution value for each the category present in the list; and (vi) identifying a total contribution value of any of the categories in the list as the consciousness affect of the first consciousness input and the second consciousness input.

In accordance with one implementation of this preferred embodiment of the present teachings, the consciousness affect of the first consciousness input and the second consciousness input is identified as the category, from the list, with highest total contribution value. In an alternate preferred implementation of this preferred embodiment of the present teachings, the consciousness affect of the first consciousness input and the second consciousness input is identified as the categories, from the list, with the highest and second highest total contribution values.

Calculation and/or visual and/or audible representation of a consciousness affect for one or more users may further comprise generating and/or visually and/or audible representing a consciousness pitch. Consciousness pitch is calculated by subtracting the second highest total contribution value from the highest total contribution value.

In yet another aspect, the present teachings provide a method of forming a group. The method comprises: (i) receiving, from a plurality of client devices, a plurality of submissions, and wherein each of the client devices is associated with one or more users and each of the submissions has at least one consciousness input such that a plurality of consciousness inputs are received from plurality of the client devices; (ii) calculating, using a server and/or the client device and based on plurality of the consciousness inputs, a consciousness affects list for plurality of the users; (iii) forming, based on one or more common aspects found in the consciousness affects list, a specific group of client devices and/or users, each one of which is associated with a submission that has at least one aspect common with a consciousness affect chosen from the consciousness affects list; and (iv) allowing sharing of information only among users within the specific group of the client devices and/or the users. In preferred embodiments of the present teachings, sharing of information among all users within the group of users is allowed.

In one implementation of the present teachings, receiving includes receiving location information associated with each of the plurality of client devices. In this implementation, further the consciousness affect is visually and/or audible presented on each of the plurality of client devices for which the common aspect is the location information.

In another aspect, the present teachings provide a method of transforming one or more shares (as will be explained in greater detail below, a share is a submission of information that is provided to other users (e.g., text, icons and/or media)) into a visual and/or audible consciousness affect representation. The method comprises: (i) retrieving or receiving, from memory of a client device and/or a server, one or more of the shares, each of which contains one or more submissions; (ii) identifying, in each of the submissions, information relating to one or more consciousness input types; (iii) extracting, from the information relating to one or more of the consciousness input types, information relating to one or more categories of each of the consciousness input types ("categories") to generate a list identifying one or more extracted categories from each of the submissions; (iv) assigning, based on an age of each of the submissions, a contribution value to each of the submissions and assigning a predetermined value to each of the extracted categories from each of the submissions; (v) determining, for each of the submissions, a submission's category contribution value, which represents a contribution of each of the submissions to each of the extracted categories present in the list, and wherein the submission's category contribution value equals a product of the contribution value and the predetermined value; (vi) adding the submission's category contribution value for each of the submissions to arrive at a total contribution value for each the category present in one or more of the shares; (vii) resolving the total contribution values of the categories present in one or more of the shares to establish the consciousness affect of one or more of the shares; and (viii) visually and/or audibly representing the consciousness affect on one or more of the client devices.

In preferred embodiments of the present teachings, one or more of the shares are retrieved or received in an analog and/or a digital state. Further, the above-mentioned step of resolving is preferably carried out in real-time, which is substantially contemporaneous with the steps of retrieving or receiving. More preferably, the steps of retrieving or receiving include retrieving or receiving an intensity information accompanying each of one or more of the submissions and the predetermined value assigned to the category at least partially depends on the intensity of the category, and wherein in absence of retrieving or receiving the intensity information, the predetermined value is assigned a default intensity value.

In preferred embodiments of the present teachings, visually and/or audibly representing the consciousness affect includes visually representing, on the client device, an illustration or photo of an object associated with the category that is identified as being the consciousness affect.

In accordance with one embodiment of the present arrangements, the list is an electronic concatenated list that includes for each of the submissions, an identification of each of the extracted categories, the predetermined value assigned to each of the extracted categories, a timestamp of the submission and an aging index that represents the age of the submission.

The method of transforming one or more shares into a visual and/or audible representation of the consciousness affect includes an optional step of filtering the concatenated list to filter out certain undesired categories and form an electronic filtered list of desired categories. Preferably, each of the submissions having a timestamp that is equal to or greater than a threshold timestamp is removed.

Another optional step of the present teachings comprises grouping each of the desired categories to form an electronic grouped list, which includes the identification of each of the extracted categories, the predetermined value assigned to each of the extracted categories and the aging index that represents the age of each of the submissions.

In certain preferred embodiments of the present teachings, the step of resolving includes identifying the total contribution value of any one of the extracted categories as being the consciousness affect of one or more of the shares. In another implementation of this embodiment, the step of resolving includes identifying a dominant category with the highest total contribution value, or the dominant category and a sub-dominant category with the highest and the second highest total contribution values, among the different total contribution values of the extracted categories, as being the consciousness affect of one or more of the shares. As a result, visually and/or audibly representing the consciousness affect, in certain embodiments, includes visually representing, on the client device, an illustration or photo of one or more objects associated with the dominant category or the dominant and the sub-dominant categories.

In certain other preferred embodiments of the present teachings, the above-mentioned step of resolving includes performing at least one activity chosen from a group comprising generating a consciousness pitch, generating an activity index and generating intensity for one or more of the shares. According to the present teachings, subtracting the second highest total contribution value from the highest total contribution value provides the consciousness pitch. The activity index is determined by dividing, for each of the shares, a total number of responses by total number of users involved to arrive at the activity index.

Calculation of intensity for one or more of the shares comprises: (i) sorting one or more of the total contribution values in descending order and establishing one of the extracted categories associated with a highest total contribution value as a dominant category; (ii) adding the predetermined values for each of the submissions that contributes to the dominant category and arriving at a total of predetermined values; (iii) adding number of submissions that contribute to the dominant category and arriving at a total number of submissions; (iv) dividing the total of predetermined values by the total number of submissions to arrive at a dominant reference value; (v) determining the intensity of one or more of the shares to be of a low value and correspondingly, visually and/or audibly representing an object of a small size or generating an audible sound of a lower volume or of a different tone, if the dominant reference value is less than the default intensity value for the dominant category; (vi) determining the intensity of one or more of the shares to be of a high value and correspondingly, visually and/or audibly representing an object of a large size or generating an audible sound of a higher volume or of another different tone, if the dominant reference value is higher than the default intensity value for the dominant category; and (vii) determining the intensity of one or more of the shares to be of a normal value and correspondingly, visually and/or audibly representing an object of a normal size or generating an audible sound of a normal volume or of yet another different tone, if the dominant reference value is substantially equal to the default intensity value for the dominant category.

Regardless of how the consciousness affect is calculated, the present teachings preferably include visually and/or audibly representing it on the client device.

A network-based system for providing a consciousness affect, the network-based system comprising: (i) a processor for executing code; (ii) memory, coupled to the processor, for storing code to be executed by the processor; (iii) at least one interface, coupled to the processor, operable to provide a communication link from the processor to one or more client devices and that is used for transmitting and/or receiving information; and wherein the processor performs operations of: (a) receiving, from a client device, a first consciousness input and a second consciousness input, wherein the client device is associated with one or more users and the first consciousness input is different from the second consciousness input; (b) calculating, using a server and/or the client device and based on the first consciousness input and the second consciousness input, a consciousness affect for one or more of the users; (c) storing, in memory of the server and/or the client device, the consciousness affect; and (d) wherein the first consciousness input includes at least one input chosen from a group comprising emotional state input, reasoned input, location information input, physical awareness input and spiritual insight input, and the second consciousness input is at least one input chosen from a group comprising reasoned input, location information input, physical awareness input and spiritual insight input.

A network-based system for providing a consciousness affect, the network-based system comprising: (i) a processor for executing code; (ii) memory, coupled to the processor, for storing code to be executed by the processor; (iii) at least one interface, coupled to the processor, operable to provide a communication link from the processor to one or more client devices and that is used for transmitting and/or receiving information; and wherein the processor performs operations of: (a) retrieving or receiving, from memory of a client device and/or a server, one or more of the shares, each of which contains one or more submissions; (b) identifying, in each of the submissions, information relating to one or more consciousness input types; (c) extracting, from the information relating to one or more of the consciousness input types, information relating to one or more categories of each of the consciousness input types ("categories") to generate a list identifying one or more extracted categories from each of the submissions; (d) assigning, based on an age of each of the submissions, a contribution value to each of the submissions and assigning a predetermined value to each of the extracted categories from each of the submissions; (e) determining, for each of the submissions, a submission's category contribution value, which represents a contribution of each of said submissions to each of the extracted categories present in the list, and wherein the submission's category contribution value equals a product of the contribution value and the predetermined value; (e) adding the submission's category contribution value for each of the submissions to arrive at a total contribution value for each the category present in one or more of the shares; (f) resolving the total contribution values of the categories present in one or more of the shares to establish the consciousness affect of one or more of the shares; and (g) visually and/or audibly representing the consciousness affect on one or more of the client devices.

In one aspect, the present arrangements provide a network-based system for forming a group. The network-based system includes: (i) a processor for executing code; (ii) memory, coupled to the processor, for storing code to be executed by the processor; (iii) at least one interface, coupled to the processor, operable to provide a communication link from the processor to one or more client devices and that is used for transmitting and/or receiving information; and wherein the processor performs operations of: (a) receiving, from a plurality of client devices, a plurality of submissions, and wherein each of the client devices is associated with one or more users and each of the submissions has at least one consciousness input such that a plurality of consciousness inputs are received from plurality of the client devices; (b) calculating, using a server and/or the client device and based on plurality of the consciousness inputs, a consciousness affects list for plurality of the users; (c) forming, based on one or more common aspects found in the consciousness affects list, a specific group of client devices and/or users, each one of which is associated with a submission that has at least one aspect common with a consciousness affect chosen from the consciousness affects list; and (d) allowing sharing of information only among users within the specific group of the client devices and/or the users.

In another aspect, the present arrangements provide one or more client devices. An exemplar client device includes: (i) a client processor for executing code; (ii) a client memory, coupled to the client processor, for storing the code; (iii) a client interface, coupled to the client processor, to provide a communication link from the client processor to at least one server; (iv) a client display interface, coupled to the client processor, for receiving input from a user of the client device and/or for displaying content to the user; wherein the client processor performs operations of: (a) receiving a request, from the user, to access services of the client processor; (b) displaying, on the client display interface, a first consciousness input icon and a second consciousness input icon; (c) wherein the first consciousness input icon includes at least one icon chosen from a group comprising emotional state input icon, reasoned input icon, location information input icon, physical awareness input icon and spiritual insight input icon, and the second consciousness input icon is at least one icon chosen from a group comprising reasoned input icon, location information input icon, physical awareness input icon and spiritual insight input icon; (d) wherein the user uses the emotional state input icon to convey an emotional state of the user, the users uses the reasoned input icon to convey a reasoned expression of the user, the user uses the location information input icon to convey a location information associated with the user, the users uses the physical awareness icon to convey physical awareness information associated with the user and chosen from a group comprising general health information, body type and biology awareness, and the user uses the spiritual insight icons to convey spiritual insight information that includes an extra sense of purpose or presence associated with the user; and (e) wherein each of the emotional state, the reasoned expression, the location information, the physical information and the spiritual insight information are different from each other.

In one embodiment of the present arrangements, the client memory has stored thereon information relating to the emotional state input icon, the reasoned input icon, the location information input icon, the physical awareness input icon, and the spiritual insight input icon.

In another embodiment of the present arrangements, the emotional state input icon, the reasoned input icon, the location information input icon, the physical awareness input icon, and the spiritual insight input icon are stored in a client module, which is part of the client device, and wherein the client module, in a connected state, couples to a server module, which is part of the server.

In accordance with one embodiment of the present arrangements, the client devices includes at least one module chosen from a group comprising geo-location module, weather determination module, motion detection module, touch detection module, speech processing module, facial recognition module and transcription processing module.

The construction and method of operation of the invention, however, together with additional objects and advantages thereof, will be best understood from the following descriptions of specific embodiments when read in connection with the accompanying figure.

BRIEF DESCRIPTION OF THE DRAWINGS

FIG. 6D shows a table containing exemplar predetermined values assigned to different degrees of intensity (i.e., less, default and more) and a rank associated with each of the different categories within location information inputs.

FIG. 6E shows a table containing exemplar predetermined values assigned to different degrees of intensity (i.e., less, default and more) and a rank associated with each of the different categories within reasoned inputs.

FIG. 7 is a table that, on one column, shows a method, according to one embodiment of the present teachings, of transforming consciousness inputs in a share into a consciousness affect that is visually and/or audibly represented on a client device and that, on another column, shows accompanying, exemplar set of instructions to implement the method.

FIG. 8A is a table showing different types of consciousness inputs, according to one embodiment of the present teachings and that may be identified in a share.

FIG. 8B shows a table including an electronic concatenating list, according to one embodiment of the present teachings and that results from a concatenating step of the method shown in FIG. 7.

FIG. 8C shows a table including a filtered list, according to one embodiment of the present teachings and that results from a filtering step of the method shown in FIG. 7.

DETAILED DESCRIPTION OF THE PREFERRED EMBODIMENTS

Figure 1A:
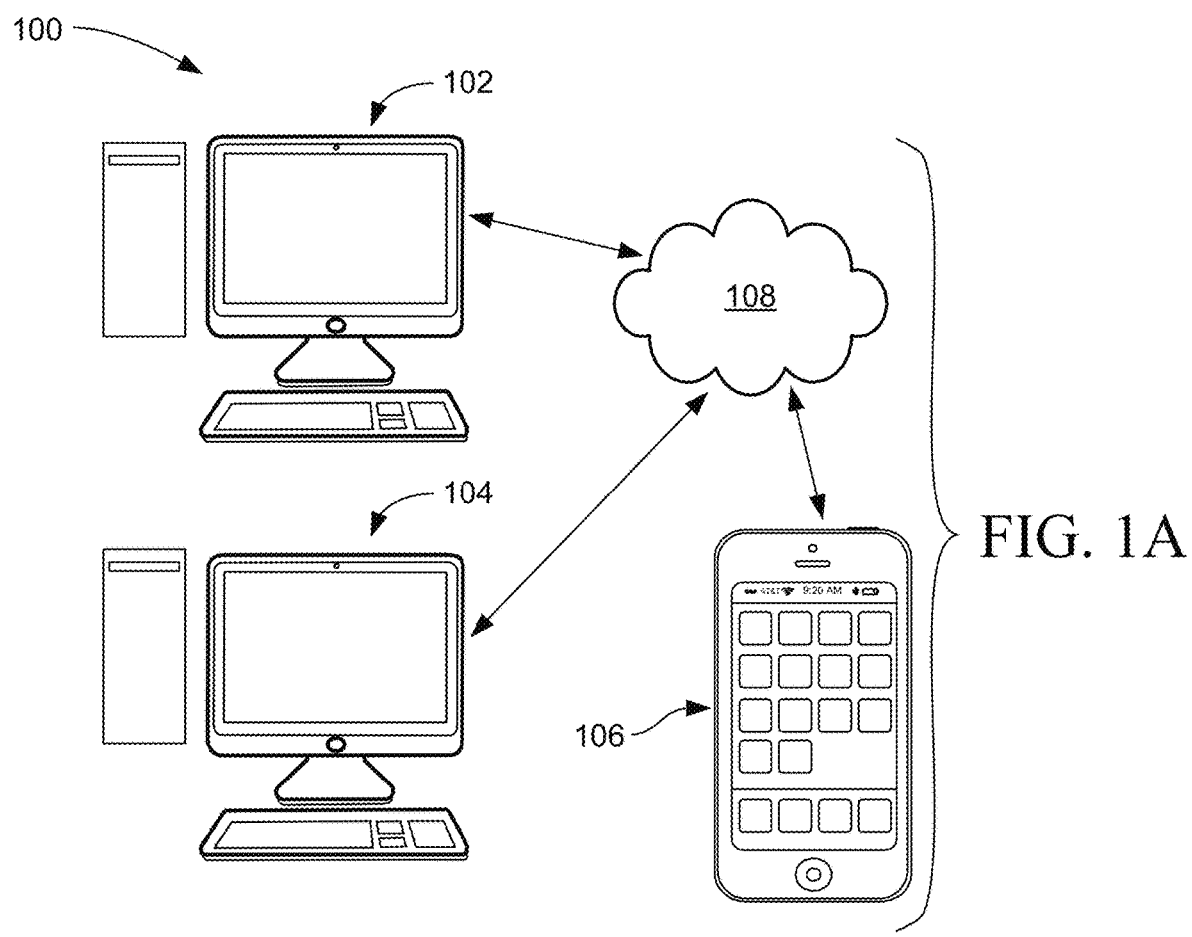
FIG. 1A shows a network platform, according to one embodiment of the present arrangements, and that couples multiple computing machines, e.g., a server and multiple client devices (e.g., a desktop computer and a mobile device) to each other for computing and/or displaying a consciousness affect.

In the following description, numerous specific details are set forth in order to provide a thorough understanding of the present invention. It will be apparent, however, to one skilled in the art that the present invention may be practiced without limitation to some or all of these specific details. In other instances, well-known process steps have not been described in detail in order to not unnecessarily obscure the invention.

The present teachings recognize that in current on-line social networks, it remains unclear how an individual influences a group, how that group responds to those influences, and vice versa. In the current Internet world, only after long time cycles, a change in individual or group thinking is identified. Moreover, it remains virtually impossible to identify all the influencing connecting thoughts that contribute to a trend. The term, "trend," or "trending," in its commonly used form, in itself implies a time-delayed indicator and is mostly based on the number or times a certain text or media appears in publication, and does not refer to the underlying consciousness affect resulting from that text or media.

Although communication is substantially immediate regardless of geography, methods used by current Internet social network services are undesirable, as they rely on a limited combination of behavioral observations. By way of example, Internet social networks frequently rely on monitoring one user's response, such as a "Like" button or a "Heart" icon, to capture the user's response to a particular content that is presented. In other words, the entire complexity of human reaction is typically deduced from a single button. The present teachings recognize that inaccuracies stemming from this limited user response is further exacerbated when the users motivations for clicking a single button or selecting a single indicator are frequently irrelevant to their real thoughts or intentions on the content they are reacting to.

To the extent certain social networking sites rely on user response to content, these sites simply tally the number of people who have hit a single button and are grossly lacking in providing insightful consumer information. In certain other instances, where there is a desire to extract a greater and/or more insightful amount of actionable consumer information, certain other sites attempt to decipher a complex pattern of emojis and text. These sites perform an analysis on complex consumer constructed emoji sequences. Unfortunately, due to different definitions of what one or more particular emojis may mean, the underlying ambiguity does not permit extraction of accurate information. Furthermore, in some instances, text may have several different meanings without understanding an author's level of linguistics and intention. As a result, based on the limited user communication collected by the current social networking sites, these sites have become ineffective for businesses to extract meaningful consumers information.

According to the present teachings, consciousness affect, preferably obtained in real-time to user input, is a mechanism that accurately identifies influences and increases understanding of consumers. Biologically, consciousness affect is calculated by the human mind at almost every moment of human life. By way of example, it is calculated while interacting with other humans when making decisions and during formation of groups. In another example, at any given moment in time, consciousness affect of the present teachings is a calculated indicator used to assess what is most likely to unfold in the physical world by the mind.

Embodiments presented herein describe systems and methods for, among other things, computing, storing and/or communicating, over a computer network, from one or more user's consciousness inputs, a consciousness affect. The systems and methods of the present teachings may be incorporated in a website or any consumer device that has access to the Internet (e.g., a client device, such as a handheld device, a laptop or a desktop computer and that are described in greater detail below) that solicits or accepts input from users. In one aspect, the present systems and methods allow visual representation of the consciousness affect on the client device.

FIG. 1A is an illustrative schematic of one embodiment of the present arrangements that includes a computer platform (hereinafter also referred to as a consciousness affect computing and/or displaying "system") 100 including multiple computing devices, shown as three exemplar machines 102, 104 and 106. In the embodiment shown in FIG. 1A, computing device 102 is a server and computing devices 104 and 106 are referred to as "client devices." A network 108 (e.g., the Internet) couples server 102 and client devices 104 and/or 106, to enable communication amongst them. As will be appreciated by those skilled in the art, any computing devices (e.g., server, desktop computer, laptop computer, tablet, or mobile device) may be used as one of server 102 and client devices 104 and 106 and configured to perform some or all of the functions contemplated in the present teachings. Furthermore, system 100 may include multiple computing machines to serve the functions of each of server 102 and each of client devices 104 and/or 106.

Representative client devices 104 and 106 (hereinafter sometimes also referred to as "user devices") include a cellular telephone, a portable digital assistant, a tablet, a stationary computing appliance, wearable computing device, a medical device for monitoring general healthcare, and/or an Internet of Things ("IoT") device. In certain embodiments of the present arrangements, each or any one of server 102 and client devices 104 and/or 106 are a wireless machine, which is in wireless communication with network 108. In this embodiment of the present arrangements, a server 102 facilitates interaction and data flows to and from any of client devices 104 and/or 106. In general, server 102 may include one or more computers and data storage devices, and may produce programming instructions, files, or data that may be transmitted over network 108 to client devices 104 and/or 106, which may be used by a user to enter a protocol, to run a protocol, including entering data, and/or analyzing data stored on server 102.

In certain embodiments of the present arrangements, as noted above, system 100 includes several components, including but not limited to a server 102 and a plurality of client devices 104 and/or 106, which are programmed to cooperatively achieve one or more of the following functions: 1) the operating of a messaging-like communication protocol (a "Messaging System") to provide content ("shares") between individual users which permits, for example, communications between a plurality of client devices 104 and/or 106 that are each typically operated by one of a plurality of users; 2) querying, through screens and input devices of client devices 104 and/or 106, a share and/or an input (hereinafter called "consciousness input") indicative of a user's or a plurality of users' consciousness state; 3) computing, based on the consciousness input of one or more users, and conveying a consciousness affect to one or more client devices or server(s); and/or 4) visually representing one or more consciousness affects one or more client devices.

In one embodiment of the present arrangements, client devices 104 and/or 106 are provided with programming that allows users to communicate with one another using a messaging system. Server 102 is an intermediary in the communication, and stores information regarding the messages. A user using one or more of computing devices 104 and 106, in certain embodiments of the present arrangements, is an individual or a representative of an individual (such as a politician or a celebrity), a fictitious person, a group, an advertiser, a health care provider, or a company. A group is a list of users that may wish to interact or communicate with each other. A group may be used to easily allow a user to distribute a share with more one or more other users that belong to that particular group. A share is a submission of information to system 100 that is provided to other users (e.g., text, icons and/or media). A share from a user may be via one of client devices 104 and/or 106. Additionally, in certain embodiments of the present arrangements, shares originate from system 100 and are transmitted to client devices 104 and/or 106. By way of example, a share from server 102 may be a location, an event, or a paid announcement.

A share, in one embodiment of the present arrangements, includes at least one of the following share elements (which may be stored by system 100): originator, share timestamp, content, consciousness input, recipients, location or event and weather. Originator refers to the source of a share. This may be a user, system 100 and/or one or more users of each client device 104 and/or 106. The share may include the user name and an image associated with the originator. Share timestamp refers to an origination time for the share. Content refers to information provided by the user for sharing with other users. The information could be, for example and without litation, a text, an image, a link, audio and/or video. Consciousness input refers to an input, using consciousness icons and degree icons (examples of which are presented below), media (e.g., audio, video, image and/or text), touch and/or movement that are provided by one or more users to reflect their consciousness states. Recipients refer to user(s) and/or one or more groups. Location or event is an optional identifier that relates the share to a physical or virtual location and/or an event. By way of example, a global positioning system ("GPS") on the client device may provide this information. Weather information for a particular location may be obtained from publicly available information such as a website. The present teachings recognize that in other embodiments, each of the above-mentioned share elements is not necessarily part of a share.

Figure 1B:
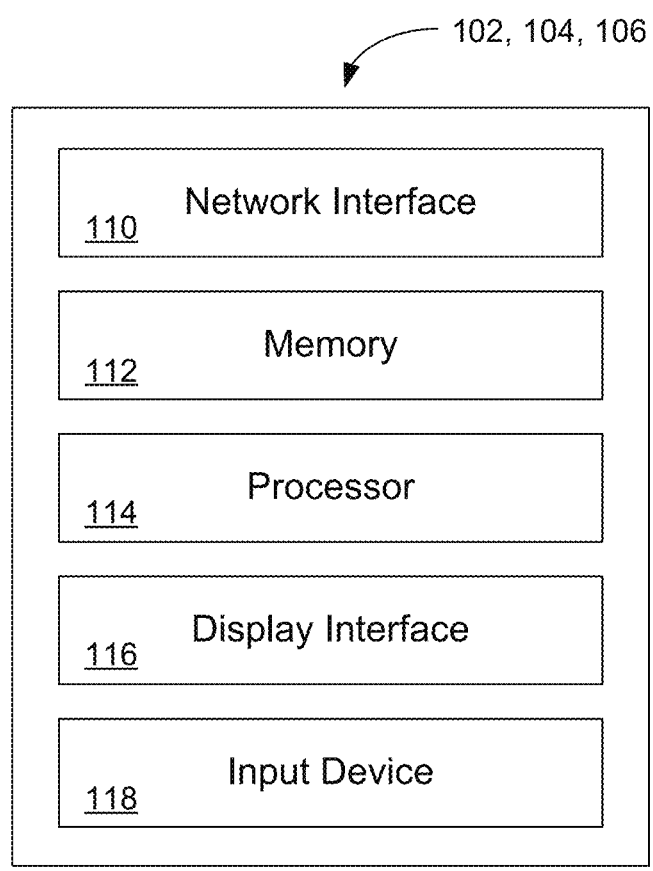
FIG. 1B shows a blocks diagram of internal components of one or more of the server and/or the client devices, according to one embodiment of the present arrangements and that is shown in FIG. 1A.

As shown in FIG. 1B, in accordance with one embodiment of the present arrangements, each of server 102 and client devices 104 and 106 include their own network interface 110, a memory 112, a processor 114, a display interface 116, and an input device 118. The present teachings recognize that the network interface 110, memory 112, and processor 114 of each of server 102 and client devices 104 and 106 are configured such that a program stored in memory 112 may be executed by processor 114 to accept input and/or provide output through network interface 110 over network 108 to another server/client device on system 100 of FIG. 1A.

Network interface 110 of each of server 102 and client devices 104 and 106 is used to communicate with another device on system 100 over a wired or wireless network, which may be, for example and without limitation, a cellular telephone network, a WiFi network or a WiMax network or a Blue Tooth network, and then to other telephones through a public switched telephone network (PSTN) or to a satellite, or over the Internet. Memory 112 of devices 102, 104 and/or 106 includes programming required to operate each or any one of server 102 and client devices 104 and/or 106, such as an operating system or virtual machine instructions, and may include portions that store information or programming instructions obtained over network 108, or that are input by the user. In one embodiment of the present arrangements, display interface 116 and input device 118 of client device 106 are physically combined as a touch screen 116/118, providing the functions of display and input.

Figure 2A:
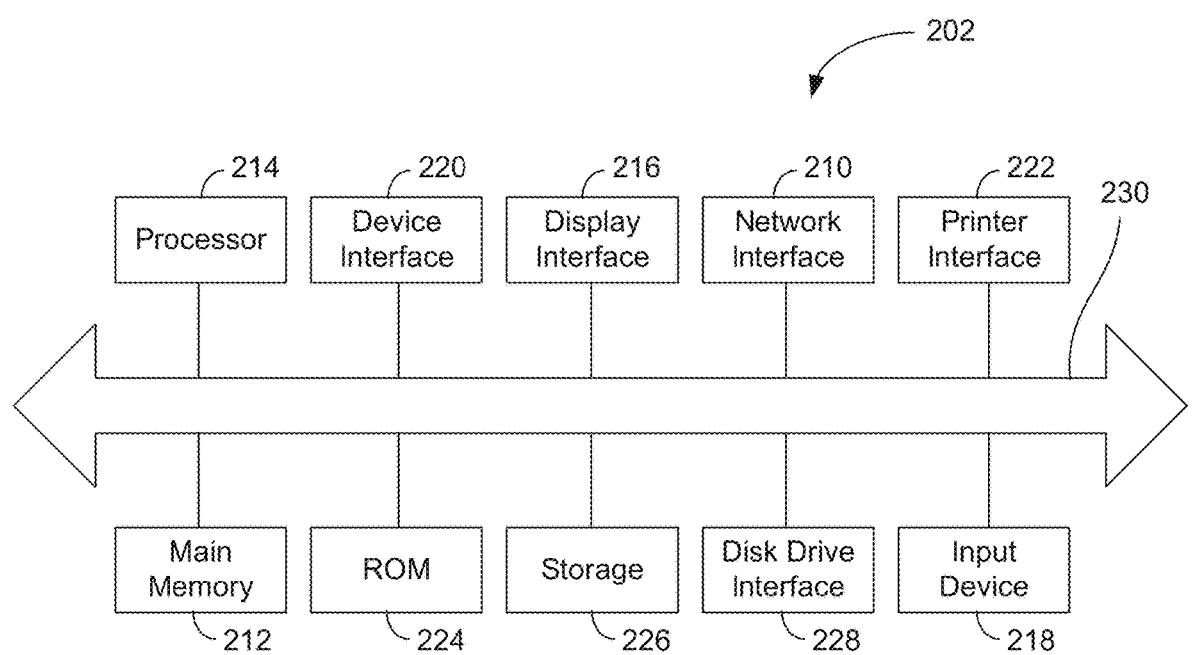
FIG. 2A shows internal construction blocks of a computing machine, according to another embodiment of the present arrangements, that may be implemented as the server shown in FIG. 1A.

FIG. 2A shows internal construction blocks of a server 202, according to one embodiment of the present arrangements and aspects of the present teachings may be implemented and executed therein. Server 202 is substantially similar to server 102 shown in FIGS. 1A and 1B. Server 202 includes a databus 230 that allows for communication between modules, such as a network interface 210, a memory 212, a processor 214, a display interface 216, and in input device 218, which are substantially similar to network interface 110, memory 112, processor 114, display interface 116, and input device 118 of FIG. 1B. Furthermore, processor 214 executes certain instructions to manage all components and/or client devices and interfaces coupled to data bus 230 for synchronized operations. Device interface 220 may be coupled to an external device such as another computing machine (e.g., server 102 and client devices 104 and/or 106 of FIG. 1A). In other words, one or more resources in the computing machine may be utilized. Also interfaced to data bus 230 are other modules such as a network interface 210, and a disk drive interface 228. Optionally interfaced to data bus 230 is a display interface 216, a printer interface 222, and one or more input devices 218, such as touch screen, keyboard, or mouse. Generally, a compiled and linked version or an executable version of the present invention is loaded into storage 226 through the disk drive interface 228, the network interface 210, the device interface 220 or other interfaces coupled to the data bus 230.

Main memory 212, such as random access memory (RAM) is also interfaced to the data bus 230 to provide processor 214 with the instructions and access to memory storage 226 for data and other instructions, applications or services. In particular, when executing stored application program instructions, such as the complied and linked version of the present invention, processor 214 is caused to manipulate the data to achieve results described herein. A ROM (read only memory) 224, which is also connected to data bus 230, is provided for storing invariant instruction sequences such as a basic input/output operation system (BIOS) for operation of display 216 and input device 218, if there is any. In general, server 202 is coupled to a network and configured to provide one or more resources to be shared with or executed by another computing device on the network or simply as an interface to receive data and instructions from a human being.

While FIG. 2A illustrates one embodiment of server 202, it should be noted that not every module shown in FIG. 2A would have to be in server 202 and/or client devices 104 and 106 in order to be used in one embodiment of the present invention. Depending on the configuration of a specific server 202 or a specific client device 104 and/or 106, some or all of the modules may be used and sufficient in one embodiment of the present invention.

Figure 2B:
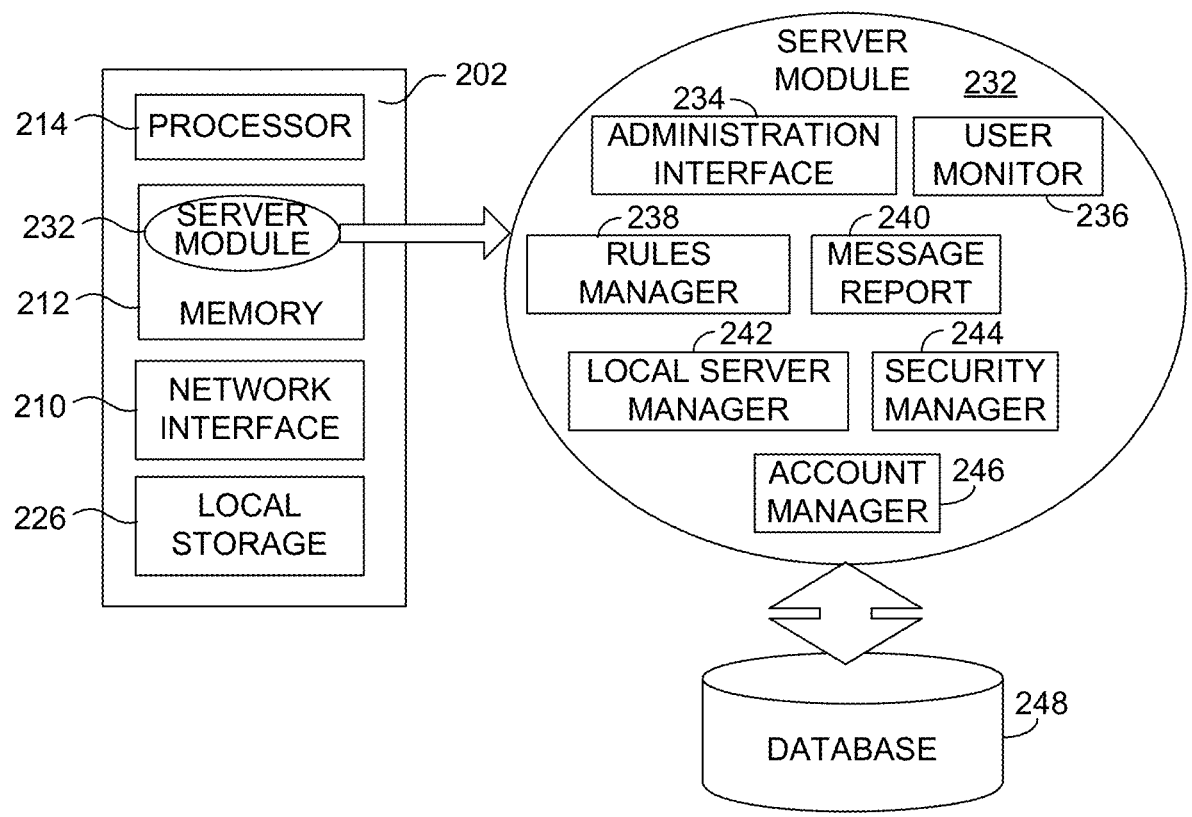
FIG. 2B shows a functional block diagram of the server of FIG. 2A, according to one embodiment of the present arrangements, and that includes a memory space, which in turn includes a server module executable by one or more processors.

Referring now to FIG. 2B, there is shown a functional block diagram of server 202, according to one embodiment of the present arrangements, in which a server module 232 resides as software in a memory 212 and is executable by one or more processors 214. According to one embodiment of the present arrangements, server module 232 is provided to memory 212 and executed in server 202 to manage various communications with the client devices 204 and/or 206 and facilitate client devices 204 and/or 206 to capture various activities by a user.

Depending on implementation, server 202 may be a single server or a cluster of two or more servers. Server 202, according to one embodiment of the present arrangements, is implemented as cloud computing, in which there are multiple computers or servers deployed to serve as many client devices as practically possible. For illustration purpose, a representative of a single server 202 is shown and may correspond to server 102 in FIG. 1A. Sever 202 includes a network interface 210 to facilitate the communication between server 202 and other devices on a network and a storage space 226. The server module 232 is an executable version of one embodiment of the present intention and delivers, when executed, some or all of the features/results contemplated in the present invention.

According to one embodiment of the present arrangements, server module 232 comprises an administration interface submodule 234, a user monitor submodule 236, a rules manager submodule 238, a message report submodule 240, a local server manager submodule 242, a security manager submodule 244, and/or account manager submodule 246. However, depending on the configuration of server module 232, some or all of the submodules components may be used.

Submodules 234, 236, 238, 240, 242, 244, and 246, when executed on processor 214, allow a user of server 202 with administrator privileges to operate server 102 to perform tasks which are generally indicated by the submodule names. Thus "administration interface" submodule 234, when executed on server 202, enables a system administrator to register [or add] a user and grant respective access privileges to the users. Administration interface submodule 234 is an entry point to server module 232 from which all sub-modules or the results thereof can be initiated, updated and managed. By way of example, user A may be allowed to enter consciousness inputs on his or her client device and receives, on the same client device, an indication of his or her consciousness affect. As another example, user B may be allowed to enter various consciousness inputs on a client device, however, the user B does not receive any indication on user B's client device. Instead, the consciousness affect is distributed to another computing device (e.g., computing device 104 of FIG. 1A) to be viewed by another user. As yet another example, a combination of the two examples presented above may be accomplished, i.e., a users consciousness affect, based on the user's consciousness inputs, is conveyed to the user and other users.

In one embodiment, an administrator sets up and manages one or more of the following processes:

The type or nature of inputs the user has access to;
Times at which the user can see or use the inputs;
The groups the user can join; and
Creating of one or more groups.

Account manager submodule 246 has access to a database or an interface to a database 248, maintaining records of registered users and their respective access privileges. Database 248 may be located on server 202 or client device 102 and/or 104. In operation, account manager submodule 246 authenticates a user when the user logs onto server 202 and also determines if the user may access other users. By way of example, when a user tries to log on to server 102, the user is prompted to input confidential signatures (e.g., username and password). Account manager submodule 246 then allows server 202 to the confidential signatures. If the confidential signatures are successfully verified, the user is authenticated and is provided access system 100. In general, account manager submodule 246 is where an operator of system 100 may be able to control its users.

Security manager submodule 244 is configured to provide security when needed. When necessary, messages, data or files being shared among registered users may be encrypted thus only authorized user may access the secured messages, data or files. In certain embodiments of the present arrangements, an encryption key to a secured file is securely maintained in the module and can be retrieved by the system administrator to access a secured document in case the key in a client machine is corrupted or the user or users who have the access privilege to access the secured document are no longer available. In another embodiment, the security manager submodule 244 is configured to initiate a secure communication session when it detects that a registered user accesses a file list remotely over an open network.

User monitor submodule 236 is configured to monitor the status of registered users and generally works in conjunction with account manager submodule 246. In particular, user monitors submodule 236 is configured to manage all registered users as a single group, respective user groups, and individual users in a private user group so that unauthorized users would not get into a group they are not permitted. In addition, user monitor 236 is configured to push or deliver related messages, updates, and uploaded files, if there is any, to a registered user.

Local server manager submodule 242, in some cases, is a collaborative communication platform that needs to collaborate with another collaborative communication platform so that users in one collaborative communication platform can communicate with users in another collaborative communication platform. In this case, a server responsible for managing a collaborative communication platform is referred to as a local server. Accordingly, local server manager submodule 242 is configured to enable more than one local server to communicate. Essentially, server 202 in this case would become a central server to coordinate the communication among the local servers.

Rules manager submodule 238 is used to configure various rules imposed across the system to control communications therein. For example, certain rules are provided to certain users that may capture displays of other client machines without asking for any permission.

A message report manager submodule 240 module is configured to record or track all messages (e.g., shares, instant messages, shared files, consciousness inputs, consciousness affects) communicated among registered users or groups of users. These messages are retained for a period of time so that a non-participated user may catch up what was communicated among the users. In one embodiment of the present arrangements, certain types of messages are kept for a predefined time in compliance of regulations or retention of evidences. In operation, message report manager submodule 240 works in conjunction with database 248 and indexes a retained message for later retrieval. In another embodiment of the present arrangements, message report manager submodule 240 is configured to record all types of events that include, but may not be limited to, a time registered user is logged onto and off the system, when an uploaded file or an share is accessed by a user.

It should be pointed out that server module 232 in FIG. 2B lists some exemplar modules according to one embodiment of the present invention and not every module in server module 232 has to be implemented in order to practice the present invention. The present teachings recognize that given the description herein, various combinations of the modules as well as modifications thereof, without departing the spirits of the present arrangements, may still achieve various desired functions, benefits and advantages contemplated in the present teachings.

Figure 3A:
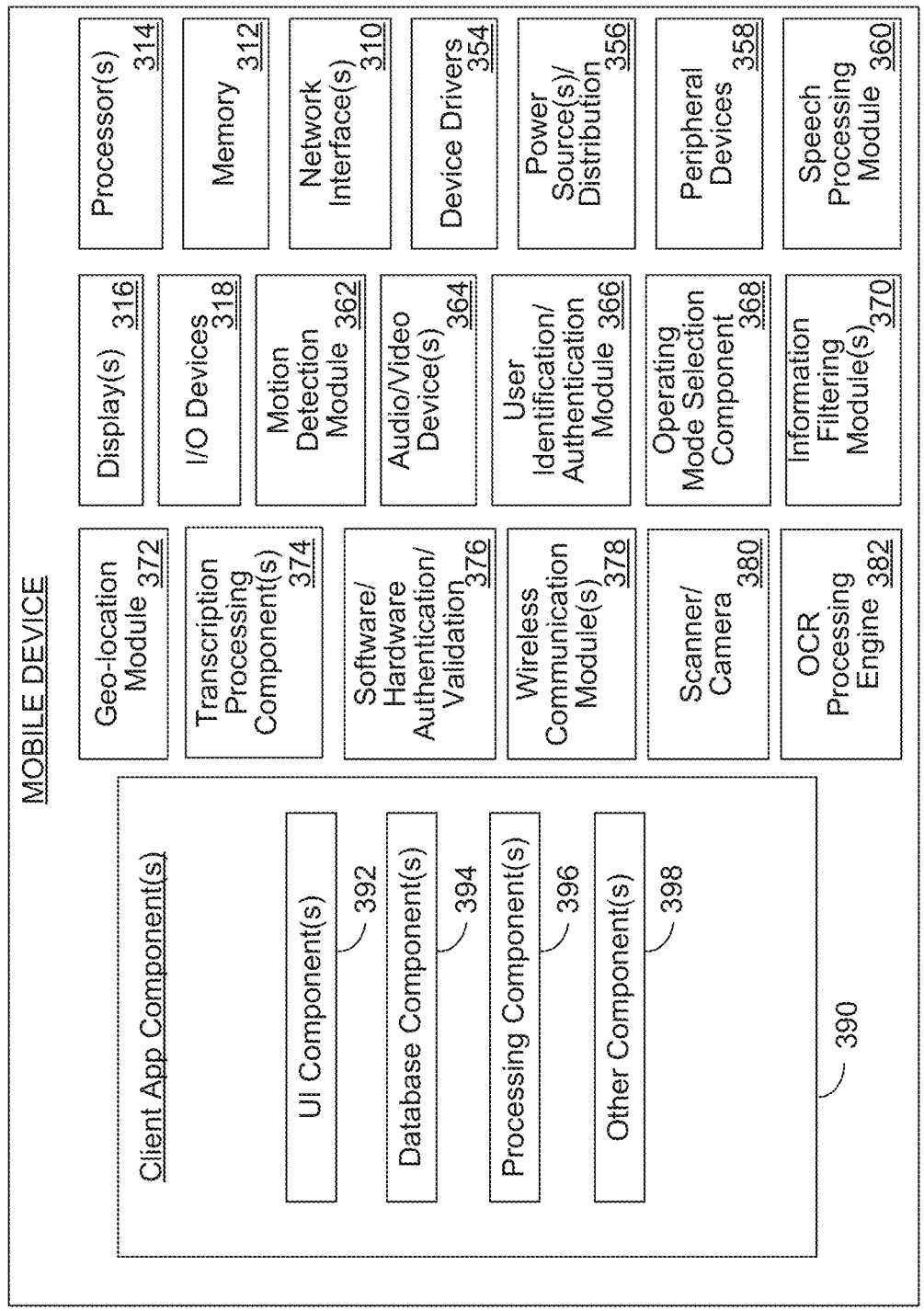
FIG. 3A shows a simplified block diagram of an exemplar client device (i.e., mobile device), according to one embodiment of the present arrangements and that is shown in FIG. 1A.

FIG. 3A is a simplified block diagram of an exemplar mobile device 306 in accordance with a one embodiment of the present arrangements. Mobile device 306 is substantially similar to client device 106 of FIG. 1A. Mobile device 306 may include consciousness affect application component(s), which have been configured or designed to provide functionality for enabling or implementing at least a portion of the various consciousness affect determination techniques at the mobile device 306. In at least one embodiment of the present arrangements, mobile device 306 may be operable to perform and/or implement various types of functions, operations, actions, and/or other features such as, for example, one or more of those described and/or referenced herein.

According to certain embodiments of the present arrangements, various aspects, features, and/or functionalities of mobile device 306 is performed, implemented and/or initiated by one or more of the following types of systems, components, systems, devices, procedures, processes, etc. (or combinations thereof):

Network Interface(s) 310
Memory 312
Processor(s) 314
Display(s) 316
I/O Devices 318
Device Drivers 354
Power Source(s)/Distribution 356
Peripheral Devices 358
Speech Processing module 360
Motion Detection module 362
Audio/Video devices(s) 364
User Identification/Authentication module 366
Operating mode selection component 368
Information Filtering module(s) 370
Geo-location module 372
Transcription Processing Component 374
Software/Hardware Authentication/Validation 376
Wireless communication module(s) 378
Scanner/Camera 380
OCR Processing Engine 382
Application Component 390

Network interface(s) 310, in one embodiment of the present arrangements, includes wired interfaces and/or wireless interfaces. In at least one implementation, interface(s) 310 may include functionality similar to at least a portion of functionality implemented by one or more computer system interfaces such as those described herein. For example, in at least one implementation, the wireless communication interface(s) may be configured or designed to communicate with selected electronic game tables, computer systems, remote servers, other wireless devices (e.g., PDAs, cell phones or user tracking transponders). Such wireless communication may be implemented using one or more wireless interfaces/protocols such as, for example, 802.11 (WiFi), 802.15 (including Bluetooth™), 802.16 (WiMax), 802.22, Cellular standards such as CDMA, CDMA2000, WCDMA, Radio Frequency (e.g., RFID) and/or Infrared and Near Field Magnetics.

Memory 312, for example, may include volatile memory (e.g., RAM), non-volatile memory (e.g., disk memory, FLASH memory, EPROMs, etc.), unalterable memory, and/or other types of memory. In at least one implementation, memory 312 may include functionality similar to at least a portion of functionality implemented by one or more commonly known memory devices such as those described herein. According to different embodiments of the present arrangements, one or more memories or memory modules (e.g., memory blocks) may be configured or designed to store data, program instructions for the functional operations of mobile device 306 and/or other information relating to the functionality of the various consciousness affect determination techniques described herein. The program instructions may control the operation of an operating system and/or one or more applications, for example.

The memory or memories may also be configured to store data structures, metadata, timecode synchronization information, audio/visual media content, asset file information, keyword taxonomy information, advertisement information, and/or information/data relating to shares and other features/functions described herein. Because such information and program instructions may be employed to implement at least a portion of the various consciousness affect determination techniques described herein, various aspects described herein may be implemented using machine readable media that include program instructions or state information. Examples of machine-readable media include, but are not limited to, magnetic media such as hard disks, floppy disks, and magnetic tape, optical media such as CD-ROM disks, magneto-optical media such as floptical disks, solid state drives, and hardware devices that are specially configured to store and perform program instructions, such as read-only memory devices (ROM) and random access memory (RAM). Examples of program instructions include both machine code, such as produced by a compiler, and/or files containing higher level code that may be executed by the computer using an interpreter.

In connection with at least one processor 314, in at least one embodiment of the present arrangements, processor(s) 314 may include one or more commonly known processors, which are deployed in many of today's consumer electronic devices. In an alternative embodiment of the present arrangements, at least one processor may be specially designed hardware for controlling the operations of mobile device 306. In a specific embodiment of the present arrangements, a memory (such as non-volatile RAM and/or ROM) also forms part of processor. When acting under the control of appropriate software or firmware, the processor may be responsible for implementing specific functions associated with the functions of a desired network device. Processor 314 preferably accomplishes one or more these functions under the control of software including an operating system, and any appropriate applications software.

In connection with one or more display(s) 316, according to various embodiments of the present arrangements, such display(s) may be implemented using, for example, LCD display technology, OLED display technology, and/or other types of conventional display technology. In at least one implementation, display(s) 316 may be adapted to be flexible or bendable. Additionally, in at least one embodiment of the present arrangements, the information displayed on display(s) 316 may utilize e-ink technology, or other suitable technology for reducing the power consumption of information displayed on the display(s) 316.

One or more user I/O device(s) 318 (hereinafter referred to as an "input/out devices(s)") provides a user to interact with mobile device 316. By way of example, input/output device(s) 318 may be chosen from a group of devices consisting of keys, buttons, scroll wheels, cursors, touchscreen sensors, audio command interfaces, magnetic strip reader, optical scanner, near field communication, a speaker to transmit an audible sound, and a microphone to receive an audio command. In another embodiment of the present arrangements, input/output device(s) 318 is a camera provided to capture a photo or video, where the data for the photo or video is stored in the device for immediate or subsequent use with other module(s) or application component 390.

In connection with device driver(s) 354, in at least one implementation, the device driver(s) 354 may include functionality similar to at least a portion of functionality implemented by one or more computer system devices such as those described herein. By way of example, display driver 354 takes instructions from processor 314 to drive display screen 316. In one embodiment of the present arrangements, driver 315 drives display screen 316 to display an image or images, a conversation between one or more users or play back a video.

At least one power source (and/or power distribution source) 356, in at least one implementation, the power source may include at least one mobile power source (e.g., battery) for allowing mobile device 306 to operate in a wireless and/or mobile environment. For example, in one implementation, the power source 356 may be implemented using a rechargeable, thin-film type battery. Further, in embodiments where it is desirable for the device to be flexible, power source 256 may be designed to be flexible.

Other types of peripheral devices 358, which may be useful to the users of various mobile devices 306, such as, for example: PDA functionality; memory card reader(s); fingerprint reader(s); image projection device(s); and social networking peripheral component(s).

Speech processing module 360 may be included, which, for example, may be operable to perform speech recognition, and may be operable to perform speech-to-text conversion.

Motion detection component 362 may be implemented for detecting motion or movement of mobile device 306 and/or for detecting motion, movement, gestures and/or other input data from user. In at least one embodiment of the present arrangements, the motion detection component 361 may include one or more motion detection sensors such as, for example, MEMS (Micro Electro Mechanical System) accelerometers, that may detect the acceleration and/or other movements of mobile device 306, as a user moves it.

Audio/video device(s) 364 such as, for example, components for displaying audio/visual media which, for example, may include cameras, speakers, microphones, media presentation components, wireless transmitter/receiver devices for enabling wireless audio and/or visual communication between mobile device 306 and remote devices (e.g., radios, telephones or computer systems). For example, in one implementation, the audio system may include componentry for enabling mobile device 306 to function as a cell phone or two-way radio device.

In one implementation of the present arrangements, user identification/authentication module 366 is adapted to determine and/or authenticate the identity of the current user or owner of mobile device 306. For example, in one embodiment, the current user may be required to perform a log in process at mobile device 306 in order to access one or more features. Alternatively, mobile device 306 may be adapted to automatically determine the identity of the current user based upon one or more external signals such as, for example, an RFID tag or badge worn by the current user, which provides a wireless signal to mobile device 306 for determining the identity of the current user. In at least one implementation of the present arrangements, various security features may be incorporated into mobile device 306 to prevent unauthorized users from accessing confidential or sensitive information.

Operating mode selection component 368, which, for example, may be operable to automatically select an appropriate mode of operation based on various parameters and/or upon detection of specific events or conditions such as, for example: mobile device's 306 current location; identity of current user; user input; system override (e.g., emergency condition detected); proximity to other devices belonging to same group or association; and proximity to specific objects, regions and zones. Additionally, the mobile device may be operable to automatically update or switch its current operating mode to the selected mode of operation. Mobile device 306 may also be adapted to automatically modify accessibility of user-accessible features and/or information in response to the updating of its current mode of operation.

Information filtering module(s) 370, which, for example, may be adapted to automatically and dynamically generate, using one or more filter parameters, filtered information to be displayed on one or more displays of the mobile device. In one implementation of the present arrangements, such filter parameters may be customizable by a user of the device. In some embodiments of the present arrangements, information filtering module(s) 370 may also be adapted to display, in real-time, filtered information to the user based upon a variety of criteria such as, for example, geo-location information, proximity to another user in a group and/or by time.

Geo-location module 372 which, for example, may be configured or designed to acquire geo-location information from remote sources and use the acquired geo-location information to determine information relating to a relative and/or absolute position of mobile device 306. Geo-location may be determined, for example, by GPS, WI-FI, or a cellular network.

Transcription processing component(s) 374 which, for example, may be operable to automatically and/or dynamically initiate, perform, and/or facilitate transcription of audio content into corresponding text-based content. In at least one embodiment, transcription processing component(s) 374 may utilize the services of one or more remote transcription servers for performing at least a portion of the transcription processing. In at least one embodiment of the present arrangements, application component 390 include a consciousness affects determination application that may initiate transcription of audio content, for example, via use of an application program interface ("API") to a third-party transcription service. In some embodiments of the present arrangements, at least a portion of the transcription may be performed at the user's mobile device 306.

In one implementation of the present arrangements, the wireless communication module 378 may be configured or designed to communicate with external devices using one or more wireless interfaces/protocols such as, for example, 802.11 (WiFi), 802.15 (including Bluetooth™), 802.16 (WiMax), 802.22, Cellular standards such as CDMA, CDMA2000, WCDMA, Radio Frequency (e.g., RFID) and Infrared and Near Field Magnetics.

Software/Hardware Authentication/validation components 376 which, for example, may be used for authenticating and/or validating local hardware and/or software components, hardware/software components residing at a remote device, user information and/or identity.

In accordance with one embodiment of the present arrangements, scanner/camera component(s) 380, which may be configured or designed for use in capturing images, recording video, scanning documents or barcodes, may be used.

OCR Processing Engine 382, which, for example, may be operable to perform image processing and optical character recognition of images such as those captured by a mobile device camera, for example.

As illustrated in the example of FIG. 3A, mobile device 306 may be implemented as a mobile or handheld computing device, which includes a variety of components, modules and/or systems for providing various functionality. For example, mobile device 306 may include application components 390, which may include, but are not limited to, one or more of the following (or combinations thereof):

UI components 392 such as those illustrated, described, and/or referenced herein.

Database components 394 such as those illustrated, described, and/or referenced herein.

Processing components 396 such as those illustrated, described, and/or referenced herein.

Other components 398, which, for example, may include components for facilitating and/or enabling mobile device 306 to perform and/or initiate various types of operations, activities, and functions such as those, described herein.

In at least one embodiment of the present arrangements, consciousness affect application component(s) 390 may be operable to perform and/or implement various types of functions, operations, actions, and/or other features such as, for example, one or more of the following (or combinations thereof):

Consciousness affects determination application 390 may be installed and operated at a user's mobile communication device such as a mobile telephone/smart phone device;

Consciousness affects determination application 390 presents configuration options, which may include, but are not limited to, hours of operation, pre-selected user's names for the use with the system, options related to time constraints associated with the application's functions and/or features, rules for selecting individual contact records, amongst other options;

Consciousness affects determination application 390 may operate continually in the background during user-specified times of operation;

In one embodiment of the present arrangements, consciousness affects determination application 390 provides an interface to collect audio recording of and/or transcription of the audio recording to text;

In one embodiment of the present arrangements, consciousness affects determination application 390 transcribes audio dictation to text locally at the mobile device;

Consciousness affects determination application 390 may assemble input data, including but not limited to, voice audio data, transcribed text data in to multiple formats, locational data, GPS data, time and date data, video and/or graphic information;

In one embodiment of the present arrangements, information may be conveyed in a variety of different electronic mediums and networks, which may include the Internet, wireless networks and/or private/proprietary electronic networks;

Consciousness affects determination application 390, in certain embodiments of the present arrangements, may be configured or designed to facilitate access to various types of communication networks such as, for example, one or more of the following (or combinations thereof): the internet, wireless networks, a private electronic networks, or proprietary electronic communication systems, cellular networks, and/or local area networks;

In one embodiment of the present arrangements, consciousness affects determination application 390 may automatically access various types of information at the user's mobile communication device such as, for example, one or more of the following (or combinations thereof): audio data, video data, motion detection, GPS data and/or user profile data;

In at least one embodiment of the present arrangements, consciousness affects determination application 390 may be operable to access, send, receive, store, retrieve, and/or acquire various types of data, which may be used at the user's mobile device and/or by other components/systems of the Consciousness Platform; and In at least one embodiment, consciousness affects determination application 390 may communicate with a computer system (e.g., computer system 100 of FIG. 1A) to automatically perform, initiate, manage, track, store, analyze, and/or retrieve various types of data and/or other information (such as, for example, emotional state inputs, reasoned inputs, location information inputs, physical awareness inputs and spiritual insights inputs) which may be generated by (and/or used by) consciousness affects determination application 390.

According to certain embodiments of the present arrangements, multiple instances of consciousness affects determination application 390 may be concurrently implemented and/or initiated via the use of one or more processors and/or other combinations of hardware and/or hardware and software. By way of example, in at least some embodiments of the present arrangements, various aspects, features, and/or functionalities of the consciousness affects determination application component(s) 390 are performed, implemented and/or initiated by one or more of the following types of systems, components, systems, devices, procedures, and processes described and/or referenced herein.

In at least one embodiment of the present arrangements, at least a portion of the database information may be accessed via communication with one or more local and/or remote memory devices (e.g., memory 212 and database 248 of FIG. 2B). Examples of different types of input data, which may be accessed by the consciousness affects determination application 390 component(s), may be chosen from a group comprising media, voice audio data, transcribed text data, GPS/locational data, touch, movement, time and date data, video and graphic information. Consciousness affects determination application 390 may also automatically obtain input data from a remote server (e.g., server 102 of FIG. 1A) or database (e.g., database 248 of FIG. 2B), including but not limited to consciousness affects.

Figure 3B:
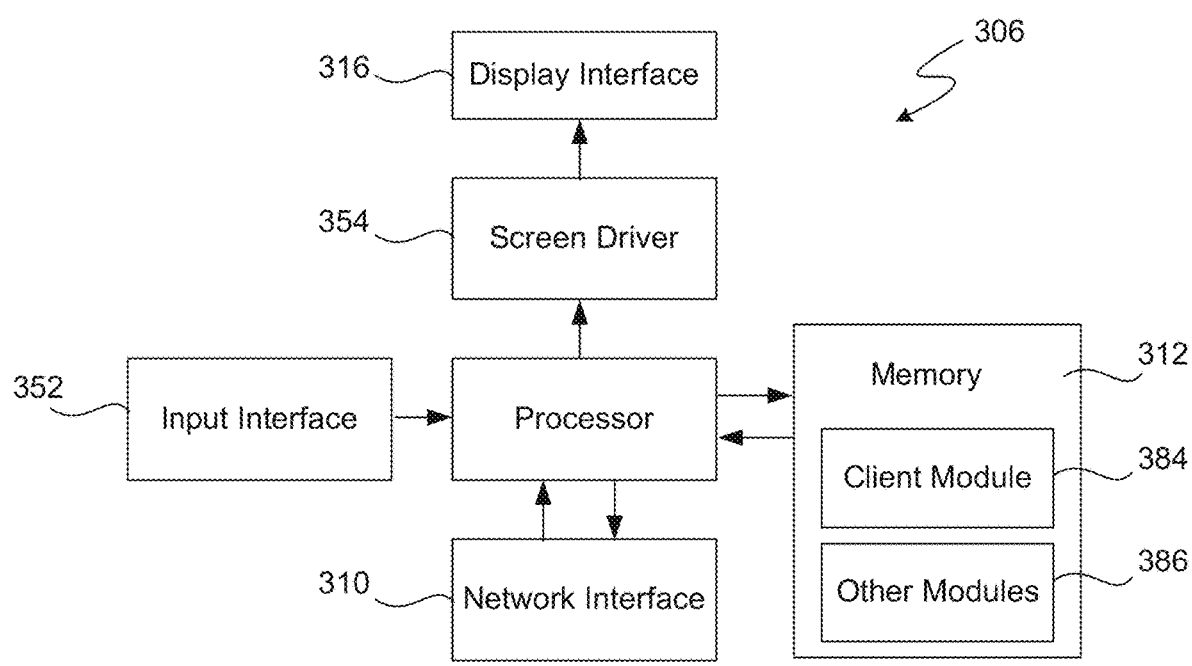
FIG. 3B shows a functional block diagram of the client device, according to one embodiment of the present arrangements, in which a client module resides in memory space of the client device shown in FIG. 1A.

Referring now to FIG. 3B, an internal functional block diagram illustrates a client device 306 that may be used with a computer system (e.g., computer system 100 of FIG. 1) according to one embodiment of the present arrangements. Client device 306 is substantially similar to client device 306 of FIG. 3A but includes a client module 384 and other modules 386. According to one implementation, client module 384 and other modules 386 are loaded in memory 312 and when executed by processor 314 delivers features, advantages and benefits contemplated by the present arrangements (e.g., have information regarding the different consciousness input icons as described in connection with 4A-4E). By way of example, client module 384, when executed by processor 314, receives a consciousness input that is processed at processor 314 and/or conveyed to a server (e.g., server 102 of FIG. 1A) to compute consciousness affects. As will be further described below, the visual representation of one or more consciousness affects may be simply viewed and interacted with.

In one embodiment of the present arrangements, client module 384 is, uniquely designed, implemented and configured to dynamically change the visual representation of a user or a group of user's state of consciousness. The present teachings recognize that the process of visually displaying a user's or a group of user's consciousness affect(s) is not something a general computer is capable of performing by itself. A general computer must be specifically programmed or installed with a specifically designed module such as the client module 312 according to one embodiment of the present invention to perform this process. To this end, in certain embodiments of the present arrangements, server module 384 of FIG. 3B and client module 232 of FIG. 2B include instructions to cooperatively achieve one or more of the following specialized functions: 1) the operating of the above-mentioned Messaging System to provide shares between individual users; 2) querying, through screens and input devices of client devices 104 and/or 106 of FIG. 1A, a share and/or a consciousness input; 3) computing, based on the consciousness input, and conveying a consciousness affect and/or a visual representation associated with it to one or more client devices or server(s); and/or 4) visually representing one or more consciousness affects one or more client devices. Moreover, in those instances when a consciousness affect is effectively generated and/or expressed on a client device in real-time, i.e., contemporaneously with the receipt of one or more shares and/or consciousness inputs, the role of a client module, as described herein, becomes significant and a general purpose computer is not capable of performing by itself.

FIGS. 4A-4I provide screenshots 400 of a user device 406, according to one embodiment of the present arrangements. User device 406 is substantially similar to user device 106 of FIG. 2B. User device 406 includes a touchscreen 401, which may be thought of as a combination of a display interface 416 and a input device 418, is substantially similar to interface 116 and input device 118 of FIG. 1B. The screenshots, shown in FIGS. 4A-4I, are exemplars of the way in which a user inputs information and that information is displayed on user device 406.

Figure 4A:
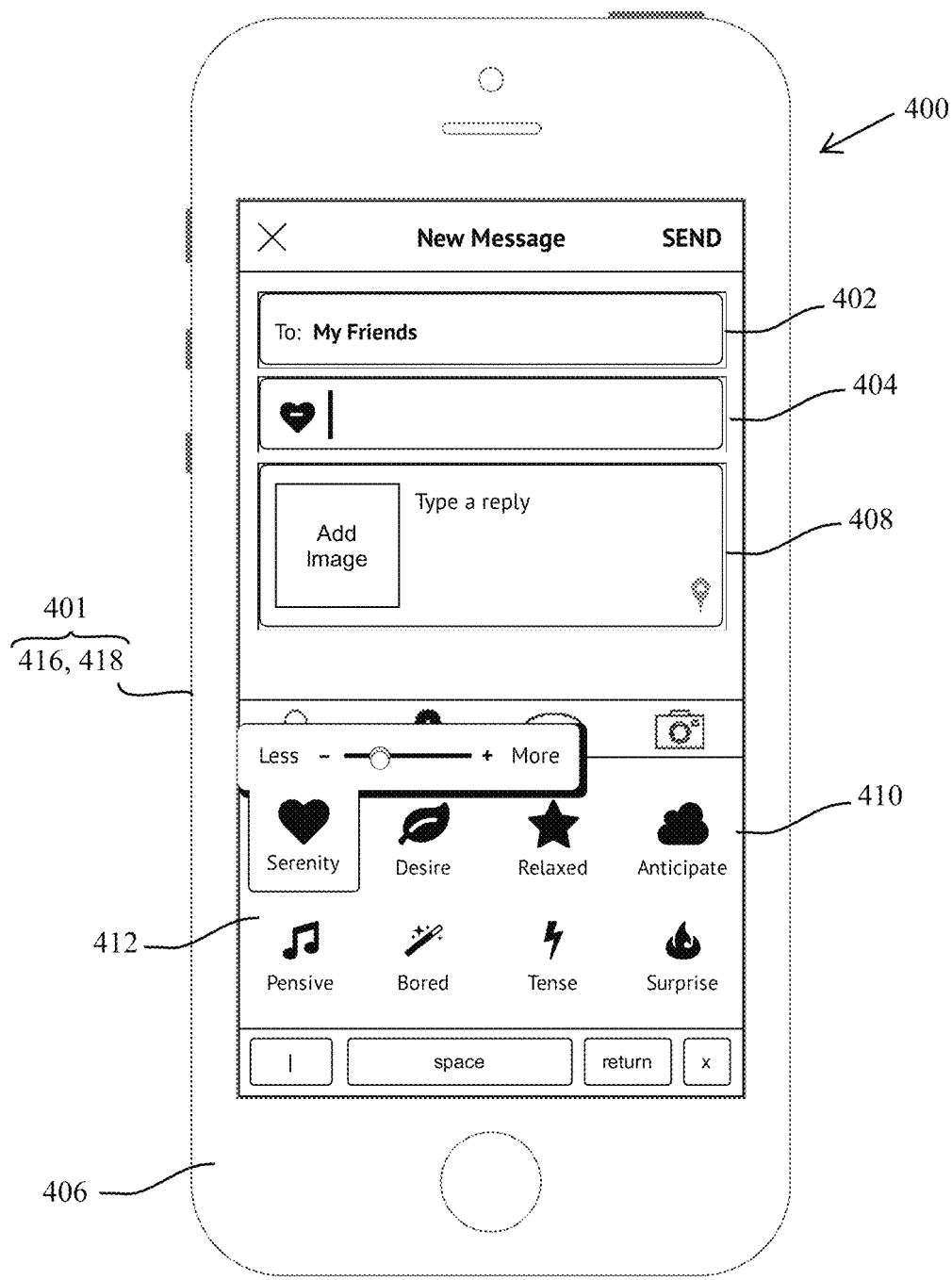
FIG. 4A shows a screenshot of a user interface, according to one embodiment of the present arrangements and that is presented, on a display screen of the client device, to receive one or more users' submissions of a share.
Figure 4B:
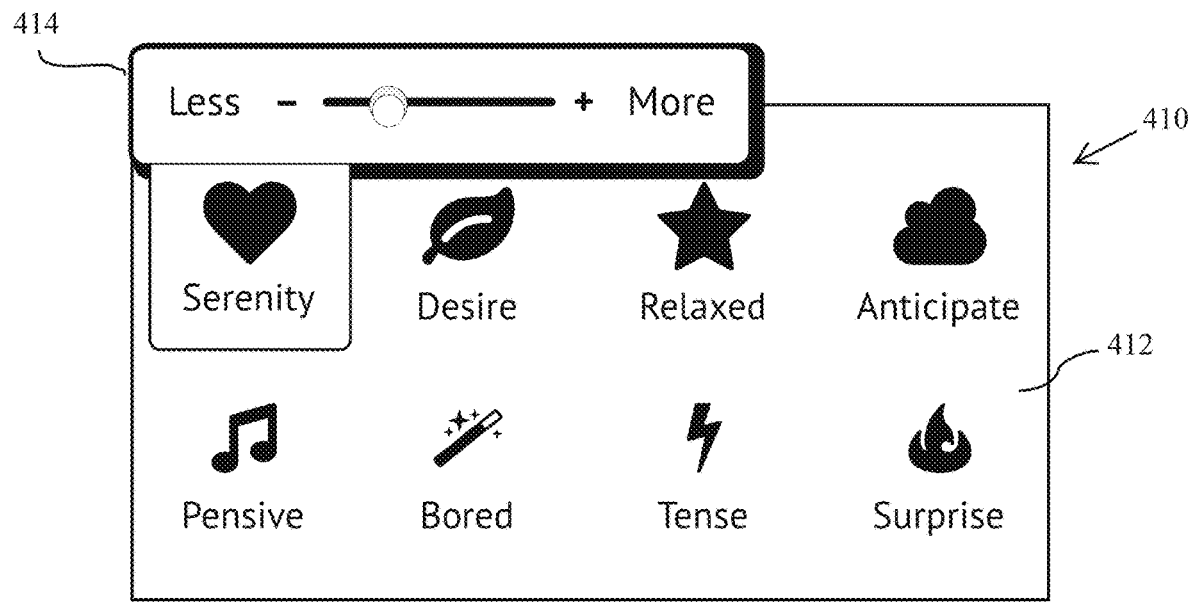
FIG. 4B shows a screenshot of a portion of the user interface, according to another embodiment of the present arrangements and that is shown in FIG. 4A and used by one or more users to input or convey certain information regarding their consciousness state and intensity associated therewith.

Screenshots 400 of FIGS. 4A and 4B are provided to a user to submit a share, according to one embodiment of the present arrangements. Touchscreen 401 receives input information about a share, including the user's consciousness state(s). Such a screenshot may be reached, for example, from a button or tab on another screen (not shown) labeled "Create Share" or by an icon or some other language indicating that the user should select that button or tab to create a new share. Screenshot 400 is shown as having a recipient input portion 402 for inputting recipients that will receive the share. Screenshot 400 further includes a consciousness input portion 404 for inputting a consciousness input and a message portion 406, if required, for providing text or media and/or for indicating a location. A typing portion 410 allows a user to fill in recipient portion 402, consciousness input portion 404 and/or message portion 406. In the example of screenshot 400, recipient input portion 402 has been provided with the user group "My Friends," which the user may have previously defined and selected from amongst the users of a System (e.g., computing system 100 of FIG. 1A), and/or message portion 408 has not yet been filled in. Further, user device 406 is configured for inputting consciousness states, and typing portion 410 has consciousness input icons 412 (e.g., icons and/or sliders) for providing consciousness state information in consciousness input portion 404.

In one embodiment of the present arrangements, the user may also assign a degree to a selected consciousness input icons 412 that is indicative of an intensity level of the consciousness input. Moving a slider (e.g., slider 414 of FIG. 4B) or selecting an icon may for example, select the degree. Examples of degrees may include—More, Normal, and Less. Thus, for example, FIGS. 4A and 4B illustrate that the user has an consciousness input corresponding to "Serenity," and a slider bar 414 appears for choosing a degree of this emotional state input.

The user may also assign a degree to selected consciousness input icons 412 that is indicative of an intensity level of the consciousness input by selecting an icon corresponding to an intensity level. In one embodiment of the present arrangements shown in FIGS. 4D and 4E, each consciousness input icon, when selected, expands to reveal three intensity icons: a less intensity icon 412A, a neutral intensity icon 412B, and a more intensity icon 412C. The intensity level of each icon is illustrated by a tilting of the icon. Shown in greater detail in FIG. 4D, neutral intensity icon 412B has a neutral orientation, less intensity icon 412A is tilted an angle, $\varphi$, to the left, and more intensity icon 412C is tilted the same angle, $\varphi$, to the right. In one embodiment of the present arrangements, the angle, $\varphi$, is about 30 degrees.

Figure 4C:
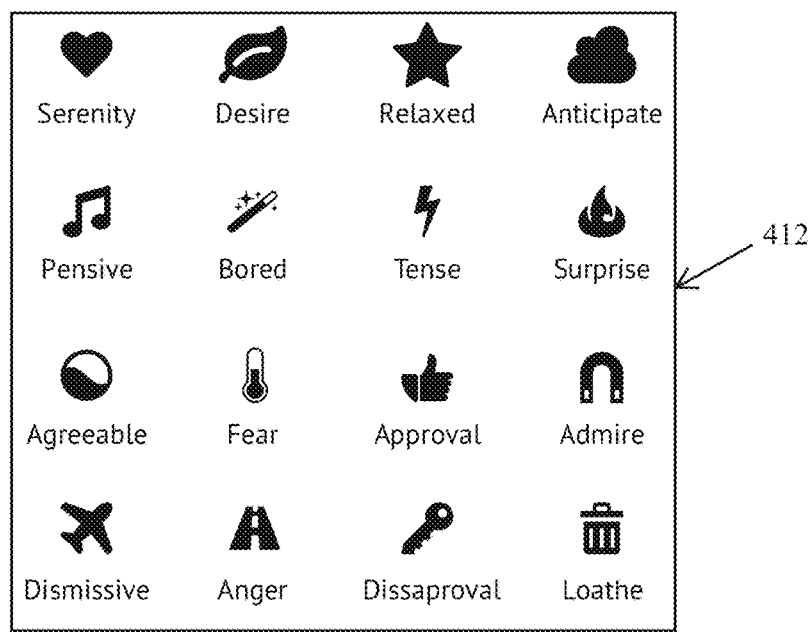
FIG. 4C shows a screenshot of another embodiment of the portion of the user interface shown in FIG. 4B and that shows certain consciousness input icons not found in the portion of user interface shown in FIG. 4B.

FIG. 4C illustrates, for example and without limitation, a list of emotional state inputs that are selectable from screenshot 400—Serenity, Desire, Relaxed, Anticipate, Pensive, Bored, Tense, Surprise, Agreeable, Fear, Approval, Admire, Dismissive, Anger, Disapproval, and Loathe. Various embodiments may have input of more, fewer, or different variations of emotions, as discussed above.

For illustrative purposes, FIGS. 4A-4E show exemplar screenshots of emotional state inputs that may be entered into consciousness input portion 404. However, the present arrangements are not so limited. Other consciousness inputs, such as reasoned input, location information input, physical awareness input and spiritual insight input, may also be entered into consciousness input portion 404 in a similar manner. In other words, in certain embodiments of the present arrangements, multiple, different consciousness states (e.g., emotional state input reasoned input, location information input, physical awareness input and spiritual insight) are entered into consciousness input portion 404. Furthermore, each consciousness state entered into consciousness input portion 404 may include multiple inputs (e.g. multiple emotional state inputs, multiple reasoned inputs, multiple reasoned inputs, multiple location information inputs, multiple physical awareness inputs and multiple spiritual insight inputs).

While not wishing to be bound by theory, the present teachings believe reasoned inputs (e.g., inputs for text, speech, audio, touch, visuals and/or taste) of a user originate from an upper portion of the user's brain (i.e., the thinking and reasoning brain that serves as a processor in the human body). The upper portion of the user's brain may be referred to as the neocortex. As a result, the present teachings believe that reasoned input may be referred to as a neocortex input or response. The emotional inputs (e.g., fear, love or joy) of a user originate from a portion of the brain below the neocortex. Origination of other types of inputs, i.e., physical awareness input, reasoned input, and spiritual insight input is not limited to only the brain. The physical awareness input, among the different consciousness inputs, provides information regarding one's general health information, body type or biology awareness. Location information input provides information regarding a location where one is present and/or represents one's response to real physical world conditions. Spiritual insight input represents or affecting the human spirit or soul as opposed to material or physical things or one's extra sense of presence or purpose. The present teachings recognize that spiritual insight input may be thought of as the soul or the "other Self."

Figures 4D, 4E:
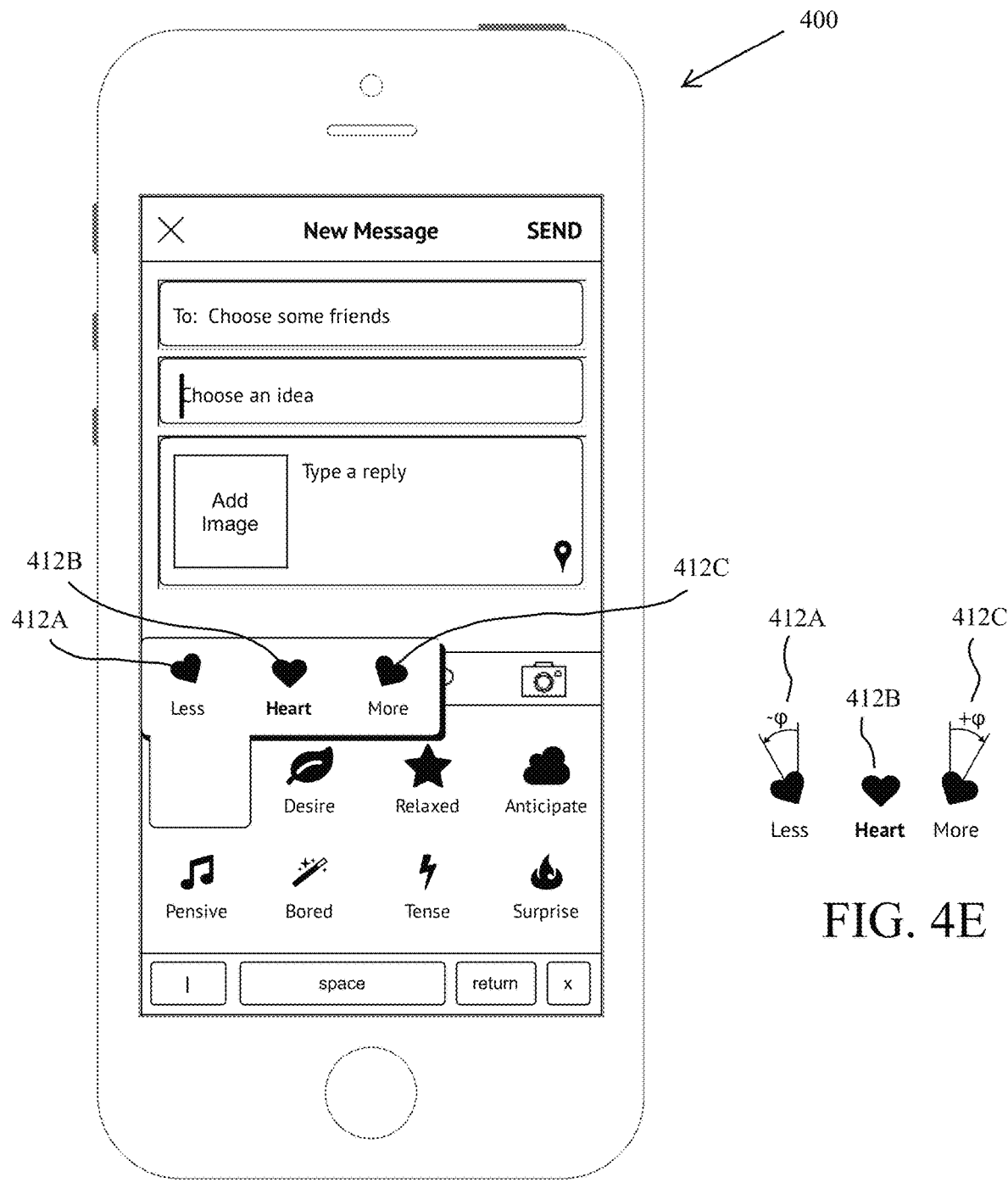
FIG. 4D shows a screenshot of a user interface, according to another embodiment of the present arrangements and that is presented, on a display screen of the client device, to receive one or more users' submissions of a share.
FIG. 4E shows multiple icons, according one embodiment of the present arrangements and that is used by one or more users to input or convey certain information regarding their consciousness state and intensity associated therewith in the portion of user interface shown in FIG. 4D.
Figure 4F:
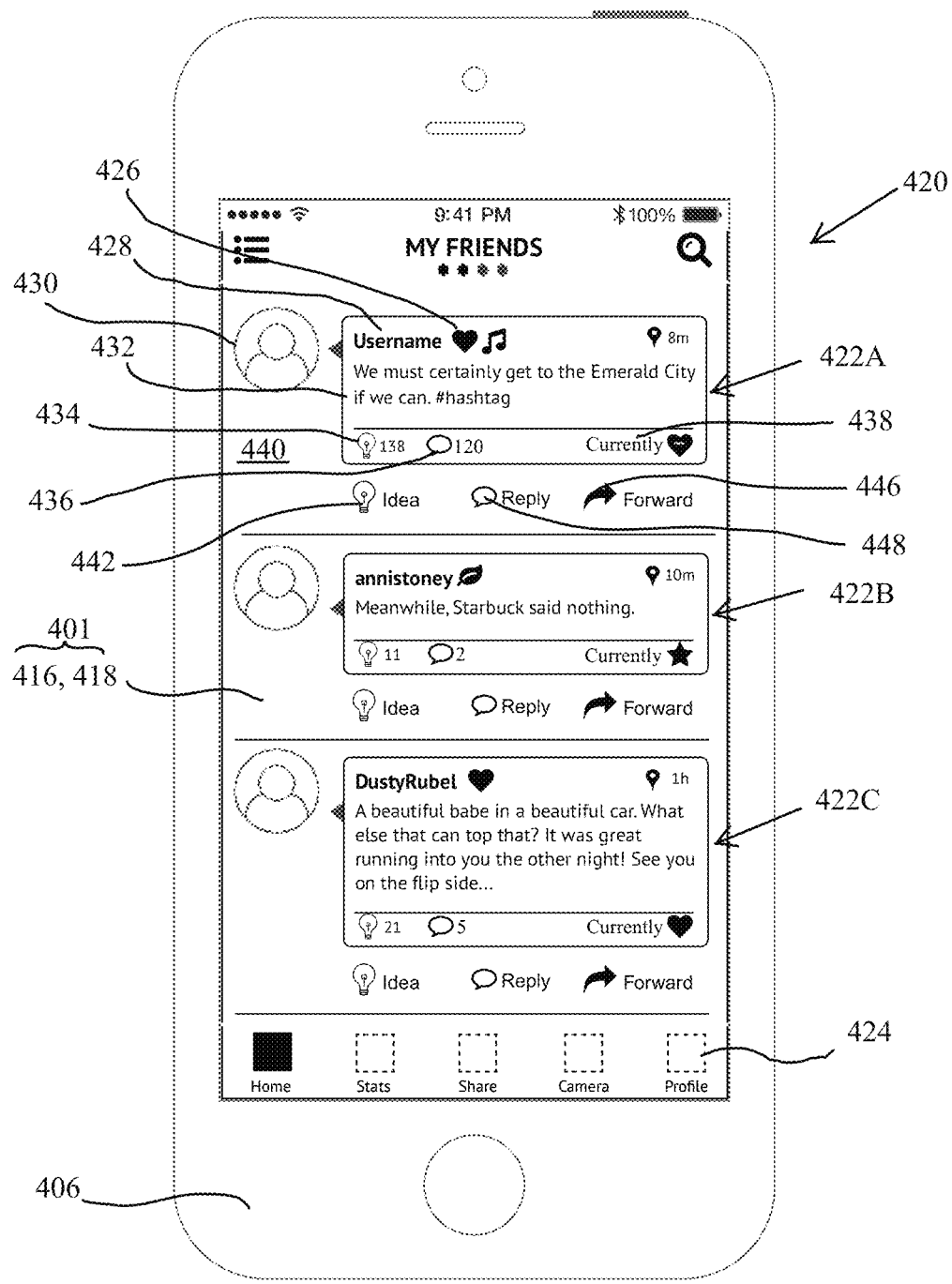
FIG. 4F shows a screenshot of a user interface, according to one embodiment of the present arrangements and that in a certain organized fashion displays multiple shares from a group of users.
Figure 4G:
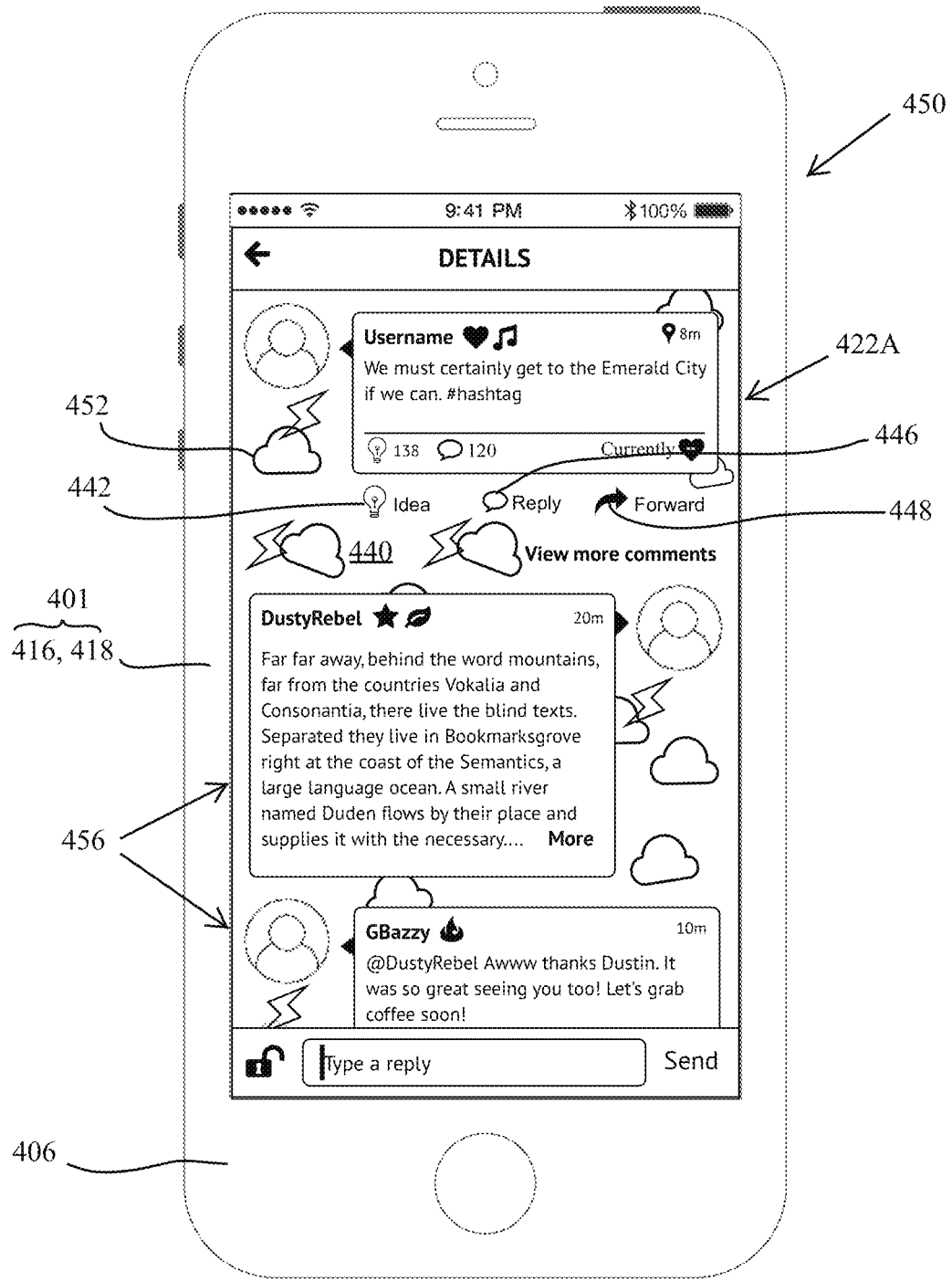
FIG. 4G shows a screenshot of a user interface, according to one embodiment of the present arrangements and that provides additional detail about a particular share chosen from the multiple shares presented in FIG. 4D.
Figure 4H:
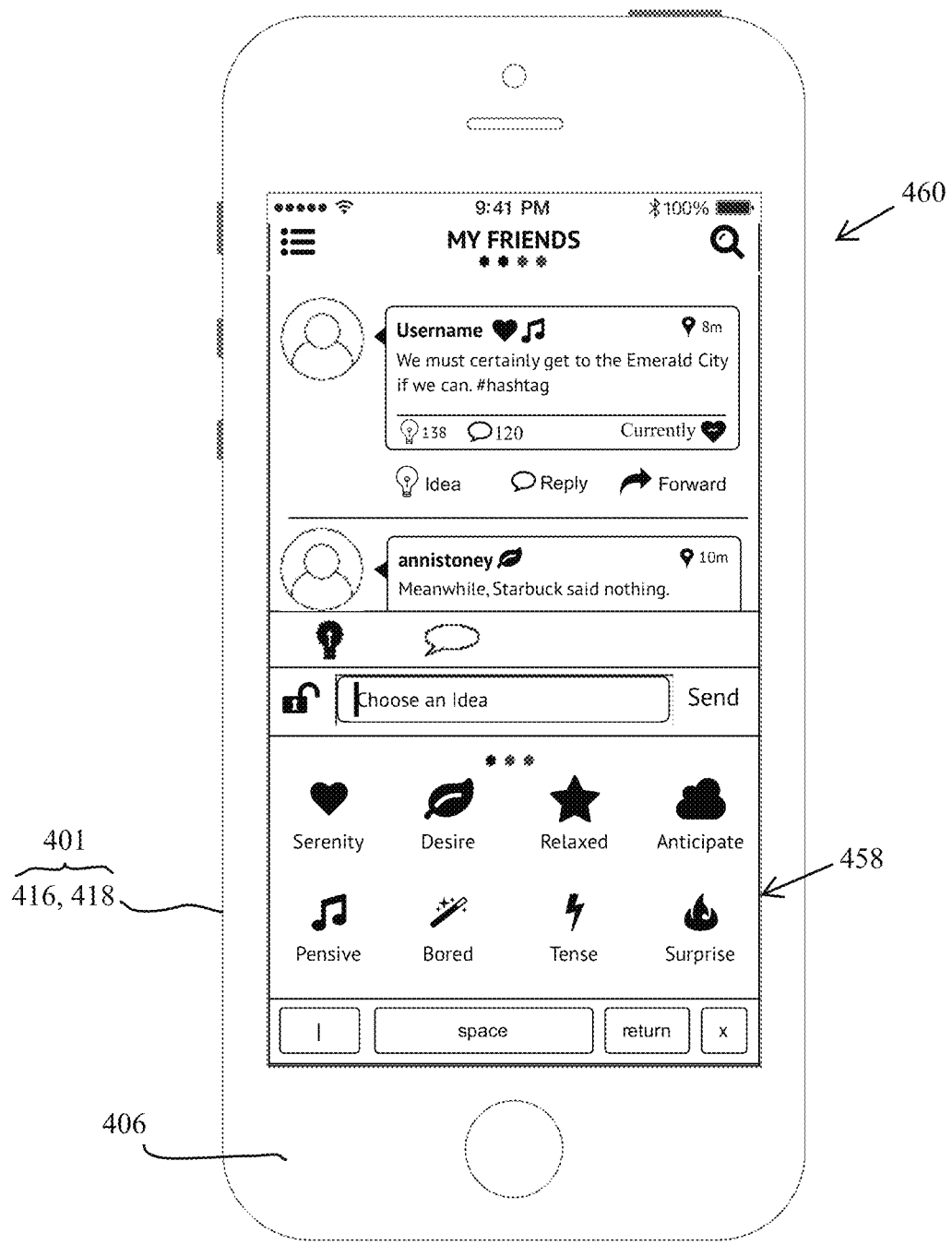
FIG. 4H shows a screenshot of a user interface, according to one embodiment of the present arrangements and that allows the user to select one or more consciousness inputs when addressing a share presented in FIG. 4D or 4E.
Figure 4I:
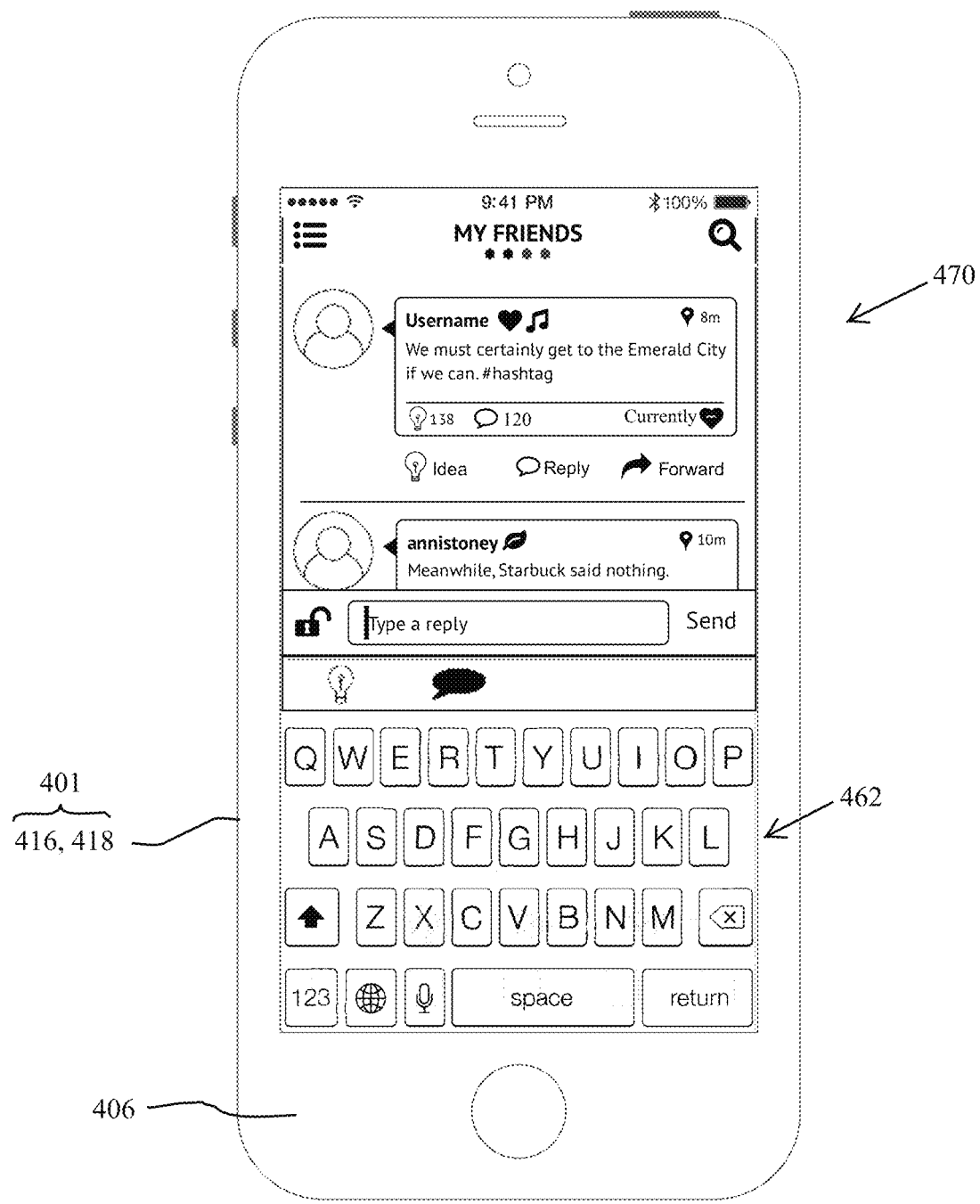
FIG. 4I shows a screenshot of a user interface, according to one embodiment of the present arrangements and that is designed to receive a user's reply to a particular share.

Screenshot 420 in FIG. 4F is representative of a screen that a user views on user device 406 for reviewing shares from the group of users that the user has defined as "My Friends." The screen includes several shares, with three shares 422A, 422B, and 422C shown as an example, and navigation buttons 424 for a home screen, to view stats, to share, to open a camera app, and to view the user's profile. Each share includes information which is shown, for example, for share 422A: a user name 428; the user's consciousness state when they constructed the share 426; a user supplied image 430; content 432 of the share (e.g., text, audio, video and/or image); the number of users that have provided a consciousness input response to the share 434; the number of users that have responded or replied to the share 436; the current consciousness affect (indicated by "Currently" in FIG. 4F) based on all responses to the share 438; and a background color 440. Additionally, button 442 may be provided for formulating a response.

In one embodiment of the present arrangements, color 440 based on a color lookup table that associates a color, which indicates the current consciousness affects based on all user responses or inputs. In certain embodiments of the present arrangement, color 440 is determined from a lookup table. See, for example, http://www.colormatters.com/color-and-design/basic-color-theory. In an alternative embodiment of the present arrangements, color 440 as a background that does not reflect consciousness affect, but is the same for each share. From screenshot 420, the user may touch an individual share as a "long hold," resulting in screenshot 450, and a change in color 440 to a color determined by the current consciousness affect.

Regardless of the different type of selections made by a user, a share may be thought of as an input packet that the user submits and that the packet includes in an integrated fashion, such discrete share components as consciousness input icons, text, audio, video and/or color background information.

The user may select one of buttons 442, 446 or 448, as discussed subsequently, or may select the share to see greater detail about the share, as shown in screenshot 450 of FIG. 4E for details on share 422A. The additional information may include a scrollable display of all responses 456 to share 422A, each including the respondent's name, consciousness input (e.g., by way of icons) in response to the share, and any comments.

In addition, a weather icon 452 (a thunder cloud, in the FIG. 4G) is provided. The weather icon 452 represents a dominant consciousness input submitted by the user or the group for the share. In an alternative embodiment of the present arrangements, the weather icon 452 is chosen to reflect a weather forecast, such as sunshine or raining, as determined from a predetermined lookup table. In the embodiment shown in FIG. 4E, for example, weather icon 452 is shown as a thundercloud, which is indicative of a negative change in consciousness state.

If the user selects button 442 from screenshot 420 of FIG. 4D or 450 of FIG. 4E, the screenshot 460 as shown in FIG. 4F is presented on device 406. Screenshot 460 shows a portion 458 for inputting consciousness inputs, as discussed above, for the share, and then pressing the "Send" button to transmit the response to a server (e.g., server 102 of FIG. 1A).

If the user selects button 448 from screenshot 420 or 450, the screenshot 460 as shown in FIG. 3G is presented on device 406. Screenshot 460 shows a portion 462 for inputting a text response to the share, and then pressing the "Send" button to transmit the response to a server (e.g., server 102 of FIG. 1A).

If the user selects button 446 from screenshot 420 of FIG. 4D or 450 of FIG. 4E, then another screenshot (not shown to simplify illustration) allows the user to input names of other users to whom the share will be forwarded.

Figure 5:
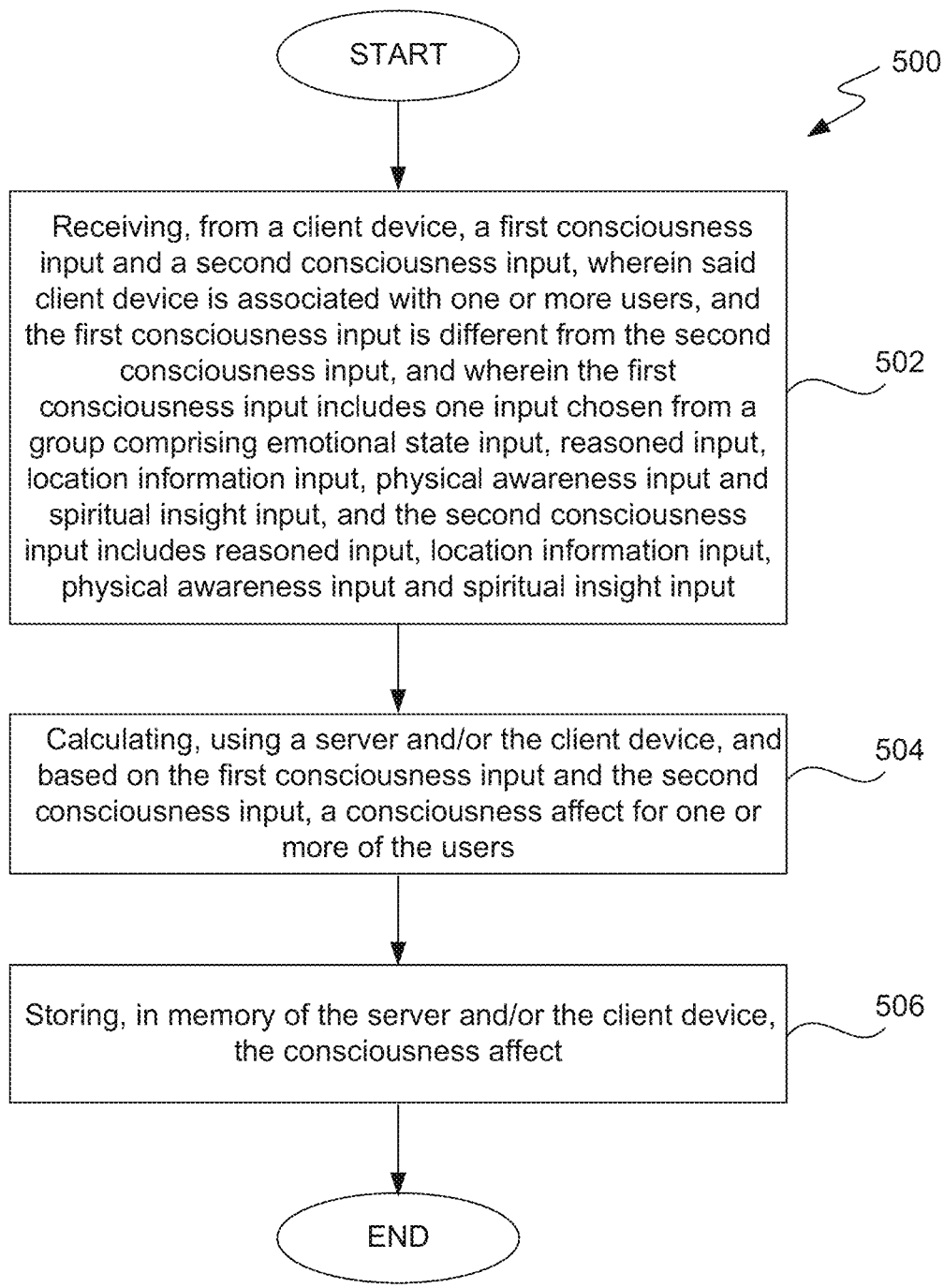
FIG. 5 shows a process flow diagram of a method, according to one embodiment of the present teachings, for transforming one or more types of consciousness inputs of one or more users into a consciousness affect that is visually and/or audibly representable on a client device.

The present teachings offer, among other things, different methods of computing and conveying consciousness affect(s) to client devices. FIG. 5 shows a method of generating a consciousness affect 500, according to one embodiment of the present teachings. Method 500 begins with a step 502, which includes receiving, from a client device, a first consciousness input and a second consciousness input. The client device is associated with one or more users and the first consciousness input is different from the second consciousness input. In this embodiment of the present teachings, the first consciousness input includes at least one input chosen from a group comprising emotional state input, reasoned input, location information input, physical awareness input, and spiritual insight input, and the second consciousness input is at least one input chosen from a group comprising reasoned input, location information input, physical awareness input, and spiritual insight input.

Next, a step 504 is carried out. Step 504 includes calculating, using a server and/or the client device and based on the first consciousness input and the second consciousness input, a consciousness affect for one or more of the users. Then, method 500 proceeds to 506. This step involves storing, in memory of the server and/or the client device, the consciousness affect of the user and/or group of users. Step 506 is optional and in certain embodiments of the present teachings, after step 504 the consciousness affect is convey and/or displayed on the client device.

Method 500 contemplates calculation of a consciousness affect for any communication medium (e.g., a share, an SMS, a text message, a chat programs, a social media program and/or a user comment sections of a website) that includes a first consciousness input and a second consciousness input. Although in method 500 the communication medium is, preferably, one or more shares, the present teachings recognize that the various steps and features are equally applicable when other communication mediums are used.

Returning to step 502, in one embodiment of the present teachings, a server (e.g., server 102 of FIG. 1A) or a client device (e.g., client device 104 and/or 106 of FIG. 1A) receives, from a client device, a first consciousness input and a second consciousness input.

A consciousness input may be any input by a user that expresses the user's consciousness state (e.g., text, icon, media, audio, image, video, touch, and/or motion). In one embodiment, a share includes, at a minimum, a first consciousness input and a second consciousness input. However, in preferred embodiments of the present teachings, a plurality of consciousness inputs are received then retrieved for processing. Regardless of whether the share includes only consciousness inputs or more information, it is typically stored in a memory (e.g., memory of the server or the client device). As a result, step 502 may include retrieving or receiving the share or information related to the share from such memory.

A user's input or message (that reflects her/his consciousness state) may be either prompted or unprompted. In the case when the user is prompted to provide a response that is insightful of his/her consciousness state, the user may receive a share from another client device and/or a request from a server. In an unprompted user's message, the user voluntarily sends a message or a share apprising of her/his consciousness state.

In either case, consciousness input information is embedded inside a user's message or share that may result from a user's selection of one or more consciousness input icons (e.g., icons 412 in FIG. 4A) and/or result from the user's submission of other share components (which are different from consciousness input icons), such as text, photo and/or audio, that reflect the user's consciousness state. If other share components, such as text, photo and/or, are embedded inside the user's share to inform on the user's consciousness state, then a preprocessing step is conducted after step 502 as explained below. If, however, the user's consciousness state is only informed by the user's selection of one or more consciousness input icons, then the preprocessing step may not be necessary. In other words, if in the user's share, the user's consciousness state information is only attributed to the user's selection of one or more consciousness input icons, then the preprocessing step may not be required.

In those instances where a preprocessing step is carried out after step 502, the share, from its integrated form, is essentially deconstructed to its discrete share components and then each of the deconstructed, discrete share component is analyzed for consciousness state information that resides therein. An exemplar preprocessing step includes identifying, as discrete items, one or more of share components from the share that they are embedded in. By way of example, the user's selection of consciousness state icons and user's text, audio and/or video embedded in the share are identified as discrete share components. Another of the optional steps includes identifying conscious state inputs from the discretely identified share components. In other words, one or more of the different types of consciousness inputs (e.g., emotional state input, reasoned input, location information input, physical awareness input and/or spiritual insight input) are extracted from the user's (selected) icons, text, audio and/or video.

By way of example, in the screenshot shown in FIG. 4A, for example, a user, conveys that—on a sunny day, he is standing at a particular location and that he feels less serene. To convey the sense of "serene" and "less," he selects the consciousness input icon "serenity" with an intensity level of "less." A preprocessing step in this example includes extracting from the entire share the consciousness input of "serenity" with an intensity level of "less."

In another example, a user's share is a text that states, "I feel sad." In this example, the preprocessing step may include analyzing the user's text and determining the user's consciousness input. In one embodiment of the present arrangements, a text-to-consciousness input module (not shown to simplify illustration) may be implemented to analyze this text. The module is stored and executed at a client device (e.g., stored in memory 312 and executed by processor(s) 214 of FIG. 3A) and/or stored and executed in a server (e.g., stored in memory 112 and executed by processor 114 of FIG. 1B). The text-to-consciousness input module analyzes the text and determines that the consciousness input is an emotional state input category of "sad."

In yet another example, a user's share includes a visual image. The user may use the client device's camera (e.g., camera 380 of FIG. 3A) to take a photo of himself/herself (i.e., "selfie") or the user my submit a preexisting image of the user or another subject's face stored in memory (e.g., memory 312 of FIG. 3A) and enter the photo into an input portion of the display screen of the client device. In one embodiment of the present teachings, a face recognition module, stored on the server or client device, may be employed to analyze the visual image. This analysis would inform on information relating to the consciousness state of the user or another subject.

In yet another example, the user's share includes an audio input. The user may speak into the user device's microphone (e.g., audio/video device 364 of FIG. 3A) or the audio input may be retrieved from memory. In one embodiment of the present teachings, a transcription module and/or component (e.g., transcription processing component 374 of FIG. 3A) transcribes the audio input into text-base content. The text may be analyzed, as described above, to determine one or more consciousness input categories. In another embodiment of the present teachings, a speech module (e.g., speech processing module 360 of FIG. 3A) is implemented to analyze the voice of the user and determine information relating to one or more consciousness inputs. In yet another embodiment of the present teachings, the audio input is transmitted to the server and the server's transcription process component and/or speech processor analyzes and/or processes the audio input.

In yet another example, a portion of the user's share is generated from the motion of the user (e.g., a users' shaking of the client device). By way of example, a motion detection module (e.g., motion detection module 362 of FIG. 3A) may detect the movement of the user device. If the motion detection component identifies that the user device is moving for a long period of time, the server may receive information relating to consciousness input category of physical awareness for "fit."

In yet another example, a portion of user's share may be based on one or more pronounced forces on input/output device 350 of FIG. 3A (e.g. keystrokes on a keyboard, mouse clicks on a mouse, or taps on a touchscreen). By way of example, the user repeatedly touches input/output device 350 and with a high degree of force provides information relating to a consciousness input category of "aggressive." By employing one or more input/output devices 350, the system (e.g., system 100 of FIG. 1) may determine a user's consciousness input by monitoring the force exercised by the user on one or more input/output devices 350.

Information relating to one or more consciousness inputs may relate to the location of the client device. A geo-location component (e.g., geo-location component 372 of FIG. 3A) on the user device determines the location of the user device. The client device and/or the server receives the geo-location, which is used to determine a location information input, from the user who confirms the location using the geo-location component. A user may also input he/her reaction to that location (e.g., location information 662 of FIG. 6D) and any of the above mentioned techniques may be used to determine a user's consciousness state, as it relates to the location of the user.

A calculating step 504 for calculating a consciousness affect, according to one embodiment of the present teachings, is substantially similar to step 704 of FIG. 7 discussed below. Step 504 includes identifying, in the first consciousness input and the second consciousness input, information relating to one or more consciousness input types (e.g., emotional state input reasoned input, location information input, physical awareness input and spiritual insight).

Figure 6A:
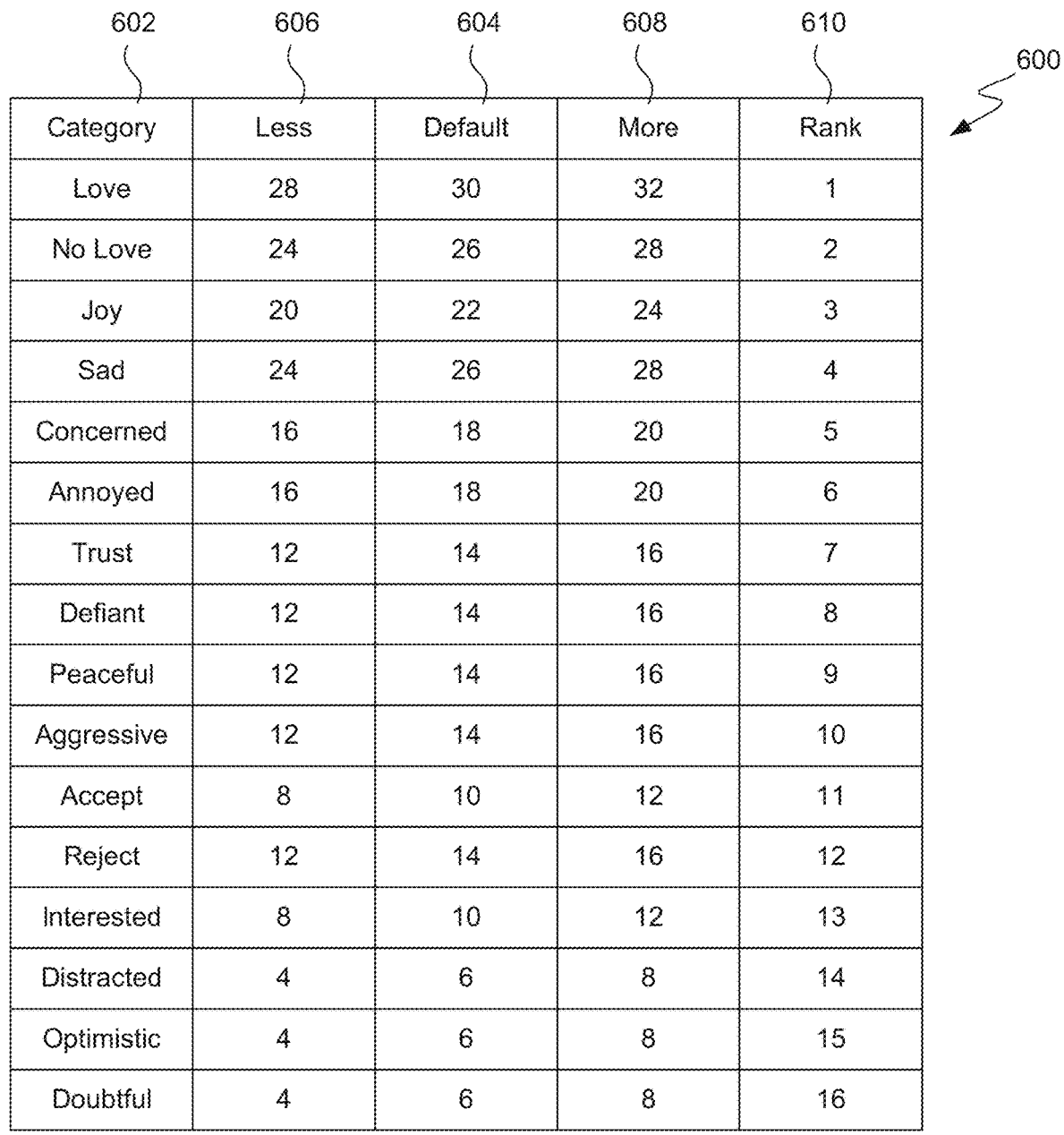
FIG. 6A shows a table containing exemplar predetermined values assigned to different degrees of intensity (i.e., less, default and more) and a rank associated with each of the different categories within emotional state inputs.
Figure 6B:
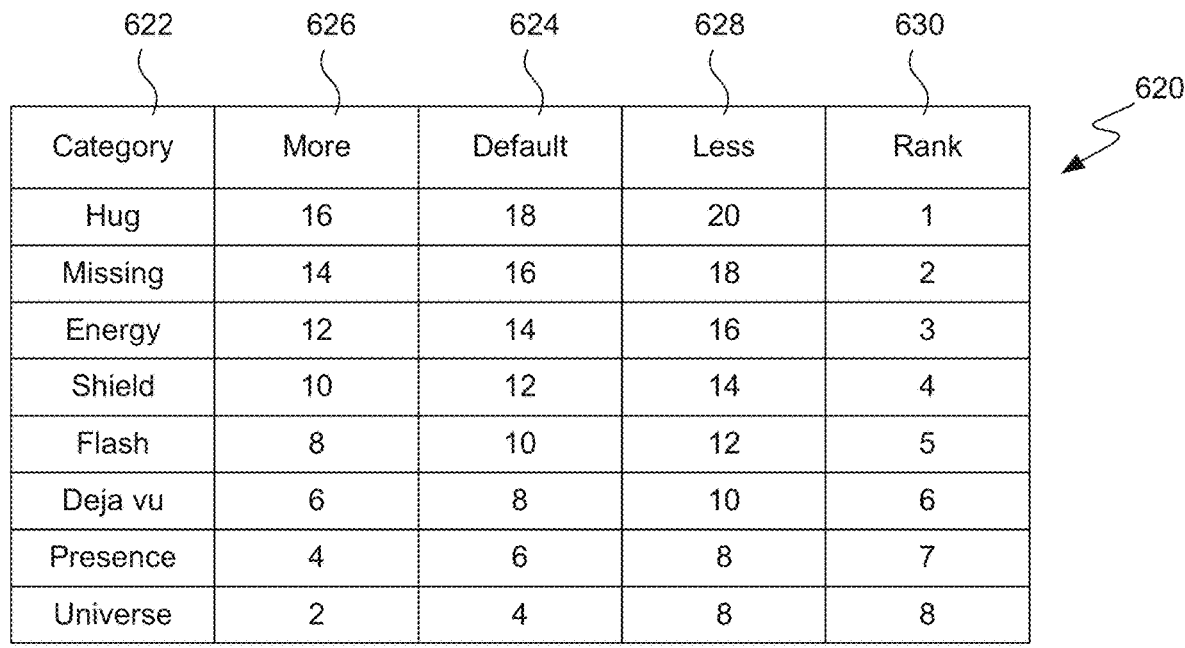
FIG. 6B shows a table containing exemplar predetermined values assigned to different degrees of intensity (i.e., less, default and more) and a rank associated with each of the different categories within spiritual insight inputs.
Figure 6C:
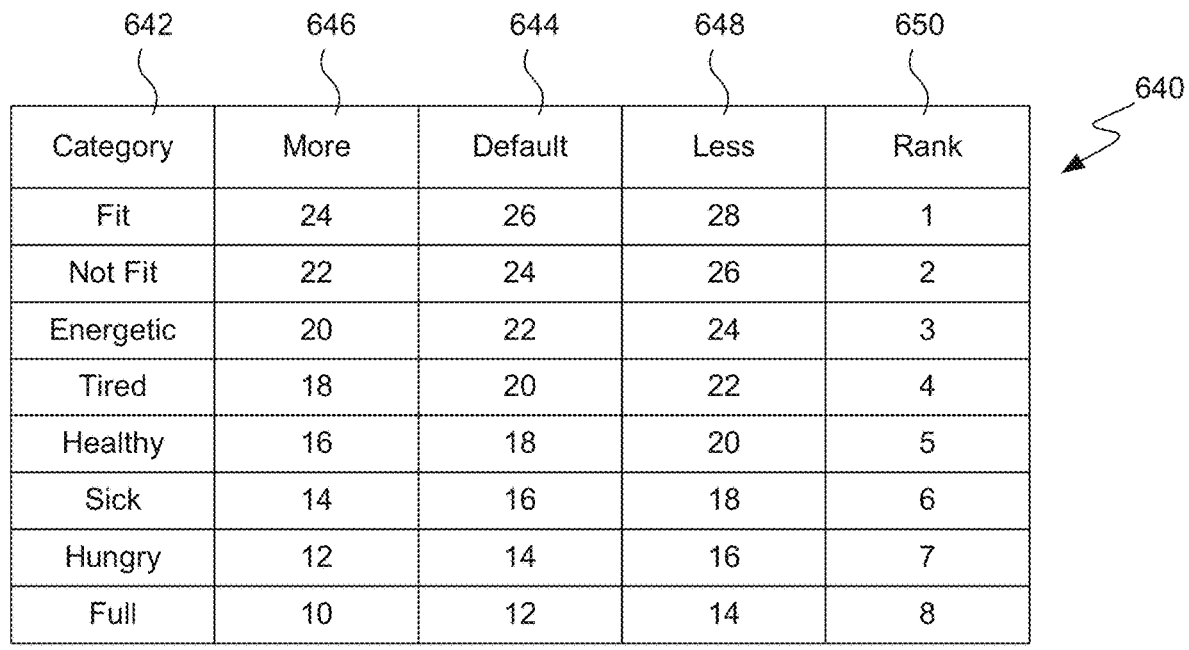
FIG. 6C shows a table containing exemplar predetermined values assigned to different degrees of intensity (i.e., less, default and more) and a rank associated with each of the different categories within physical awareness inputs.

Another step includes extracting, from the information relating to one or more of the consciousness input types, information relating to one or more categories of each of the consciousness input types ("categories") to generate a list identifying one or more extracted categories from each of the consciousness input and the second consciousness input. Each extracted category is then assigned a predetermined value. As shown in FIGS. 6A-6E, each consciousness input type includes multiple categories. FIG. 6A shows that emotional state input 600 includes the following categories shown in column 602—love, no love, joy, sad, concerned, annoyed, trust, defiant, peaceful, aggressive, accept, reject, interested, distracted, optimistic and doubtful. FIG. 6B shows that spiritual insight input 620 includes the following categories shown in column 622—hug, missing, energy, shield, flash, déjà vu, presence, and universe. FIG. 6C shows that physical awareness input 640 includes the following categories shown in column 642—fit, not fit, energetic, tired, healthy, sick, hungry and full. FIG. 6D shows that location information input 660 has the following categories shown in column 662—attraction, repulsion, calm, unrest, anticipate, remember, solitude, and congestions. FIG. 6E shows that reasoned input 680 includes the following categories shown in column 682—understand, solve, recognize, sight, hear, smell, touch and taste.

In certain embodiment of the present teachings, the predefined value for a category varies depending on an associated intensity level (i.e., less (e.g., 608, 628, 648, 668, and 688), default (e.g., 604, 624, 644, 664, and 684), and more (e.g., 606, 626, 646, 666, and 668) all of which are shown in FIGS. 6A-6E) that is specified by the user. FIGS. 4A and 4D show an exemplar user interface, which receives a user's intensity information from icons that are associated with one or more user selected categories. In other embodiments of the present teachings, such intensity information may be obtained from other media that is different than the icons associated with categories. If the intensity level of the extracted category is absent, the intensity level is set to the default intensity level (default intensity levels, e.g., 604, 624, 644, 664, and 684 shown in FIGS. 6A-6E).

To calculate consciousness affect, another assigning step, in addition to the assigning step above of predetermined values, is carried out. In this step, based on an age of the first consciousness input, a first contribution value is assigned to the first consciousness input. Similarly, based on an age of the second consciousness input, a second contribution value is assigned to the second consciousness input. The term "contribution value," as used in connection with FIG. 5, carries the same meaning as the term "aging index," used in connection with FIGS. 7 and 8A-8G.

Figures 8D, 8E, 8F, 8G:
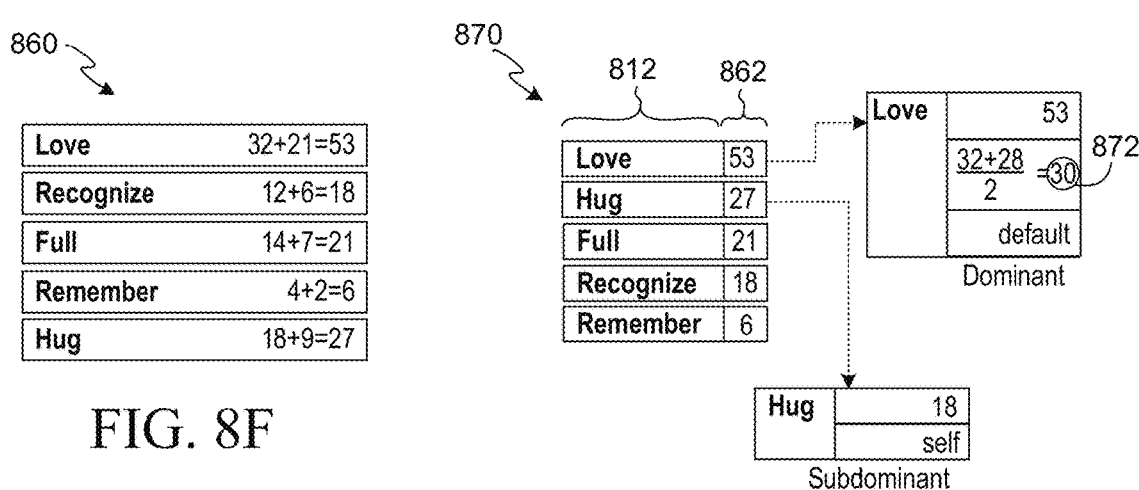
FIG. 8D shows a table including a grouped list, according to one embodiment of the present the teachings and that results from a grouping step of the method shown in FIG. 7.
FIG. 8E shows a table including an intermediate list, according to one embodiment of the present the teachings and that presents the calculation carried out in a calculating step of the method shown in FIG. 7.
FIG. 8F shows a table including a contribution list, according to one embodiment of the present the teachings and that results from the calculating step of FIG. 7.
FIG. 8G shows a table expressing a consciousness affect, according to one embodiment of the present teachings and that represents a dominant consciousness type in the share mentioned in FIG. 7.

Then, these values (i.e., predetermined value and first contribution value or second contribution value) are used to calculate a category contribution value. A category contribution value represents a contribution of the first consciousness input and, preferably, its associated first intensity information, or represents the second consciousness input and, preferably, its associated second intensity information for each of the extracted categories. The category contribution value of the present teachings is calculated by computing a product of the predetermined value (assigned to each of the extracted categories) and the first contribution value (contribution based on the age of the first consciousness input) or the second contribution value (contribution based on the age of the first consciousness input). This step is explained in greater detail below in connection with step 714 of FIG. 7 and is also shown in FIG. 8E.

Before arriving at the conscious affect of the present teachings, each category contribution value obtained above is added to arrive at a total contribution value for each of the extracted categories. A list of total contribution values for each of the extracted categories (in the first consciousness input and the second consciousness input) comprises a consciousness affect list. As will be explained later, resolving the different total contribution values results in a consciousness affect that is visually and/or audibly representable on a client device.

In one embodiment of the present teachings, the category, in the consciousness affect list, with highest total contribution value is deemed to be the consciousness affect of the first consciousness input and the second consciousness input. In another embodiment of the present teachings, two categories, in the consciousness affect list, with highest and the second highest total contribution values are deemed to be the consciousness affect of the first consciousness input and the second consciousness input. The present teachings recognize that in the example of FIG. 5, two consciousness inputs are considered, the present teachings are not so limited, and a plurality of consciousness inputs may be similarly processed to arrive at a consciousness affect for the plurality of consciousness inputs. Furthermore, certain different aspects of consciousness affects that are visually displayed are described in connection with FIGS. 9A and 9B.

A step 506 includes storing, in memory (e.g., server memory 212 of FIG. 2A and/or client device memory 312 of FIG. 3A), the consciousness affect. In certain embodiments of the present teachings, method 500 further comprises conveying the consciousness affect from the server to the memory of the client device (e.g., memory 312 of client device 306 of FIG. 3A). In another embodiment of the present teachings, the system (e.g., system 100 of FIG. 1A) may invite a user to join a community or group.

Preferably, calculating step 504 is carried out in real time, which is contemporaneous with receiving step 502. In other words, calculating the consciousness affect occurs as quickly as the first consciousness input and the second consciousness input are received. In this embodiment, the calculation of consciousness affect is limited by a processing speed of the server or the client device, on which the different consciousness inputs are being processed.

Consciousness affects are visually and/or audibly represented on a client device in a number of different ways. Representative manners of representing consciousness affect include using at least one of color, weather pattern, image, animation, textures or patterns and/or sound. Furthermore, visual and/or audio representations may change over time as one or more new consciousness inputs of one or more users are received. Each of these consciousness inputs are considered "new" as they are received later in time than, and are new relative to, the first and the second consciousness inputs.

As mentioned above, consciousness affect may also account for location information provided by the user. The user may obtain or verify his own knowledge of such information from at least one of satellite, global positioning system ("GPS"), 802.11 ("WiFi"), sensor, and radio frequency. Based on a plurality of users' consciousness inputs that identify a particular common location, (e.g. sporting event, concert venue, park, restaurant, amusement park, city, town, national monument), system 100 of FIG. 1A and/or method 500 may calculate a collective consciousness affect for that user group and that is associated with the particular location. By way of example, users visiting Yosemite National Park ("Yosemite") may provide their consciousness inputs including their location information. Using this information, the systems and methods of the present teachings visually and/or audibly present a collective consciousness affect to all the visiting users at Yosemite. In this example, the consciousness inputs are any inputs (e.g., media inputs regarding their consciousness state) relating to their experience at Yosemite.

In another embodiment of the present teachings, a collective baseline consciousness affect is identified for one or more users, at a particular location, and for a particular point in time (e.g., at a particular minute, hour, day, week, month, decade or century). Relying on such baseline consciousness affect, another user may decide to visit that particular location. By way of example, a user may want to visit Yosemite, but does not wish to visit when the park is too crowded. The user may, at his request, receive visual and/or audible information, on the client device, representing the collective baseline consciousness affect associated with Yosemite at different times. Such visual and/or audible information allows the user to gain insight into time of year, e.g., particular date/time in November, when the collective baseline consciousness affect shows that "solitude" or "peaceful" were the dominant categories. Thus, the user may choose to visit Yosemite at a particular time during November to avoid crowds.

The present teachings recognize that the calculation for the collective consciousness affect is substantially similar to the calculation of the consciousness affect. The different lists of consciousness affects for different users are integrated to form a single consciousness affects list. This integrated list, like the original consciousness affects list, contains total contribution values, from which at least one of dominant, sub-dominant, consciousness pitch, consciousness activity index and/or consciousness intensity is determined. Regardless of the type of chosen consciousness affect(s), the consciousness affect is displayed on the client device.

The server and/or client device may similarly establish a baseline consciousness affect for one or more users, based on their different consciousness affects, at a particular location. Using this information, one user may determine if another user's consciousness state deviated from the baseline consciousness affect for the particular location. By way of example, a patient visiting a doctor's office may have a baseline consciousness affect representing the category of "trust." If, after a doctor's visit, the patient conveys a consciousness affect representing the category "defiant," then the doctor's office may reach out to the patient to determine if they could further help the patient to restore his trust in the doctor or the personnel at the doctor's office.

The present arrangements and teachings recognize that different consciousness inputs may be of the same type or of different types. By way of example, if a first consciousness input type is an emotional state input, then the second consciousness input type may be a non-emotional state input, i.e., a reasoned input, a spiritual insight input, a location information input, or a physical awareness input. In another example, if the first consciousness input type is a reasoned input, then the second consciousness input type may be an emotional state input, a spiritual insight input, a location information input or a physical awareness input. In another example, if the first consciousness input type is a spiritual insight input, then the second consciousness input may be an emotional state input, a reasoned input, a location information input or a physical awareness input. In yet another example, if the first consciousness input type is a location information input, then the second consciousness input type may be an emotional state input, a reasoned input, a spiritual insight input or a physical awareness input. In yet another example, if the first consciousness input type is a physical awareness input, then the second consciousness input type may be an emotional state input, a reasoned input, a spiritual insight input or a location information input.

In connection with the embodiments where the consciousness inputs are of the same type, the two inputs are preferably chosen from a group comprising emotional state input, reasoned input, spiritual insight input, location information input, and physical awareness input. In certain preferred implementations of these embodiments, the consciousness inputs (which may be derived from shares) are processed according to the teachings provided in connection with FIGS. 4A-4I, 5, 6, 7, 8A-8G, 9A, 9B and 10.

In certain other preferred embodiments of the present teachings, where only two consciousness inputs of the same type are being processed for consciousness affect determination, the two inputs are preferably chosen from a group comprising reasoned input, spiritual insight input, location information input and physical awareness input. By way of example the first consciousness input and the second consciousness input may both be reasoned inputs, where the first consciousness input is of the category—"understand" and the second consciousness input is of the category—"recognize."

The present arrangements and teachings also provide systems and methods for transforming one or more shares into a visual and/or audible consciousness affect representation on the client device, respectively. FIG. 7 shows an exemplar method 700 for transforming one or more shares into a visual and/or audible consciousness affect representation. Method 700 beings with a step 702 that involves retrieving or receiving, from a memory of a client device and/or a server, one or more shares. Each share contains one or more submissions. Next, a step 704 is carried out. Step 704 includes identifying, in each of the submissions, information relating to one or more consciousness input types. Method 700 proceeds to step 706, which involves extracting, from the information relating to one or more of the consciousness input types, information related to one or more categories (of each of the consciousness input types). Preferably step 706 results in a list that identifies one or more extracted categories from each of the submissions.

Next, a step 708 includes concatenating the information relating to one or more of the categories to form an electronic concatenated list of categories (hereinafter referred to as the "concatenated list"), which is explained in greater detail below. After step 708, a step 710 includes filtering the concatenated list to filter out certain undesired categories and form an electronic filtered list of desired categories (hereinafter referred to as the "filtered list"). Next, a step 712 includes grouping information relating to desired categories to form one or more electronic grouped lists, each of which contains desired information regarding a single category that is found in the filtered list. Then, a step 714 includes calculating a total contribution value for each of the grouped lists to arrive at an electronic contribution list, which shows one or more total contribution values for one or more of the shares and is discussed in greater detail with respect to FIGS. 8E and 8F. Finally, a step 716 includes generating a consciousness affect for one or more of the shares. In other words, this step involves resolving one or more of the total contribution values, obtained in step 714, into a consciousness affect of one or more of the shares. Although the steps of FIG. 7 are described in terms of processing shares, these steps may also be used to process one or more consciousness inputs, such as those described in connection with FIG. 5.

In one embodiment, step 702 of the present teachings, is performed in a manner that is substantially similar to step 502 of FIG. 5. In another embodiment, step 702 of the present teachings is performed by retrieving or receiving, from sever and/or client device memory, one or more shares based on a predefined criterion. This criterion may be saved in a server and/or client device memory and/or processor. By way of example, under one criterion, a particular user's single share is retrieved to determine the consciousness affect for that share. In another example, under another criterion, one or more shares of a particular group (i.e., see "groupId(id)" of step 702 of FIG. 7).

In one embodiment, step 704 of the present teachings analyzes the discrete share components in each of the shares to determine the presence of consciousness inputs. Examples of discrete share components include consciousness state icons, media, user's text, audio, touch, motion and/or video. The analysis in this step uses one or more modules, such as a speech-to-consciousness state module and/or a facial recognition module, to identify the presence of different types of consciousness inputs. The speech-to-consciousness state module analyzes a user's text input to identify consciousness input types in the text. The facial recognition module identifies consciousness input types from an image of the user's face or another subject's face. The present teachings recognize that other off-the-shelf modules are similarly used to analyze different types of discrete share components and obtain different types of consciousness inputs present therein. FIG. 8A shows an electronic table 800, according to one embodiment of the present teachings, showing the different consciousness input types (e.g., emotional state input, reasoned input, location information input, physical awareness input and/or spiritual insight input) that may be identified in a share.

In connection with steps 706 and 708 of FIG. 7, FIG. 8B shows a resulting concatenated list 810, which identifies one or more of the extracted categories in column 812 from each of the submissions present in one or more of the shares (that are being analyzed for a consciousness affect). Concatenated list 810 also provides, for each submission, a predetermined value in column 814 that is associated with each of the extracted categories, a timestamp in column 816 that relates to the time of origin of each submission, and an aging index in column 818 for each submission based on the age of the submission. Each of the predetermined values in column 814, which are also discussed above in relation to FIGS. 6A-6E, is attributed to a particular category and preferably varies, depending on a user's indication of the intensity associated with that particular category. In one embodiment of the present teachings, a submission's aging index is assigned a value of 100%, when the age of the submission is in a range of between about 0 days and about 31 days, is assigned a value of 75%, when the age of the submission is in a range of between about 31 days and about 63 days, is assigned a value of 50%, when the age of the submission is in a range of between about 64 days and about 183 days, and is assigned a value of 0%, when the age of the submission is above 183 days.

Referring back to each submission's timestamp in column 816, timestamp refers to the time difference between the time or origination of a user's submission and when a share containing that user's submission was retrieved from memory in step 702 of FIG. 7. As explained below, timestamp in column 816 shown FIG. 8 of each submission is relevant if a filtering step 710 is carried out.

Optional filtering step 710 removes, from concatenated list 810, all submissions having a timestamp greater than or equal to a threshold timestamp, which may be any reasonable value for the timestamp. By way of example, FIG. 8C shows a filtered list 820 resulting after removing submissions have a timestamp greater than or equal to 183 days. Furthermore, filtered list 820 is substantially similar to concatenating list 810 as it includes identification of each of the extracted categories in column 812, the predetermined value in column 814, the timestamp in column 816, and the aging index in column 818. The present teachings recognize that filtered list 820 need not include timestamp in column 816.

FIG. 8D shows an example of one or more grouped lists 830, which includes a grouped list 832 for the category of "hug," a grouped list 834 for the category of "recognize," a grouped list 836 for the category of "full," a grouped list 838 for the category of "remember," and a grouped list 840 for the category of "love." Each submission within grouped list 832, 834, 836, 838, and 840 includes predetermined values in their respective column 814 and aging index in their respective column 818. By way of example, contents in grouped list 832 for "hug" were part of a first submission 842 and part of a second submission 844. Both submissions 842 and 844 were part of one or more shares that are being analyzed for consciousness affect determination. In this example in FIG. 8D, first submission 842 is assigned a predetermined value of 18 and has an aging index of one hundred percent. Similarly, second submission 844 is also assigned a predetermined value of 18 and has an aging index of fifty percent.

As mentioned before, step 714 of FIG. 7 includes, using the predetermined value and the aging index of each of these submissions, to arrive at a total contribution value for each of the grouped lists (e.g., grouped lists 832, 834, 836, 838, and 840 of FIG. 8E). Specifically, for each grouped list, FIG. 8E presents an electronic intermediate list 850, which illustrates that the predetermined value is multiplied by the aging index to arrive at a submission's category contribution value. For the first submission 842, the submission's category contribution value is 18 (i.e., 18×100%=18) and for the second submission 844, the submission's category contribution value is 9 (i.e., 18×50%=9). As a result, for the category of "hug," FIG. 8E shows submissions' category contribution values of 18 and 9. In a similar manner, the grouped lists for each of the remaining categories (e.g., grouped list 834 for "recognize," grouped list 836 for "full," grouped list 838 for "remember," and grouped list 840 for "love" shown in FIG. 8E) are processed to provide the submissions' category contribution values for each of the extracted categories present in one or more shares being analyzed for the consciousness affect determination.

FIG. 8F shows a contributions list 860, which shows the total contribution value for each of the extracted categories. As shown in this figure, each submission's category contribution value for a particular grouped list is added together to arrive at a total contribution value for each of the extracted categories. By way of example, group list 832 for "hug" has a total contribution value of 27 (i.e., 18+9=27). Thus, total contribution value of 27 for "hug" is obtained from the contribution of two submissions 842 and 844 shown in FIG. 8E. Accordingly, total contribution value is the sum of all submission's category contribution values that are associated for one or more desired categories present in one or more shares being analyzed for consciousness affect determination.

FIG. 8G shows a consciousness affect list 870, according to one embodiment of the present teachings and that lists total contribution values for the each of the categories present in one or more shares. The consciousness affect may be any one of the, or multiple categories, that have the highest total contribution value or the highest and the second highest total contribution values. In the example of FIG. 8G, the category of "love" has the highest total contribution value of 53 and is, therefore, considered the dominant category. The category "hug" has the second highest total contribution value and is, therefore, considered the sub-dominant category. Thus, in one embodiment, the consciousness affect of the present teachings is "love," and in another embodiment, it is "love" and "hug."

The present teachings also provide guidance on how to select a dominant category when two or more categories, of the same consciousness type, have the same total contribution value. According to one embodiment the present teachings, when two or more categories of the same consciousness type have the same total contribution value, a category rank (e.g., category rank 610, 630, 650, 670, and 690 of FIGS. 6A-6E) associated with each of the categories is used to determine which category is the dominant category. The category with the highest rank is the dominant category and the category with the second highest rank is the sub-dominant category. Referring again to FIG. 8G, for example, if consciousness affect list 870 included an additional spiritual insight category of "energetic" (which is not shown in FIG. 8G to simplify illustration) having a rank of 3 and a total contribution value of 53. In this situation, even though "love" (having a rank of 1) and "energetic" have the same total contribution value of 53, "love" is the dominant category because it has a higher rank (i.e., a rank of 1 is higher than a rank of 3) than "energetic."

In other embodiments of the present teachings, each of the different consciousness input types are also assigned ranks so that if two or more categories from different consciousness input types have the same total contribution values, then the category with the highest consciousness input type rank is deemed the dominant category and the category with the second highest consciousness input type rank is deemed the sub-dominant category.

A consciousness affect, however, is not limited one or more categories shown in electronic consciousness affect list 870. Rather, the consciousness affect of the present teachings may include additional or different aspects of information. In a preferred embodiment, the consciousness affect of the present teachings for one or more shares includes three aspects of different information: a dominant category; an intensity of the dominant category; and an activity index of one or more of the shares undergoing processing. As explained above, the dominant category has the highest total contribution value. The activity index for each of the shares is total number of responses in a share divided by total number of users involved in the share.

In one embodiment of the present teachings, the intensity of the dominant category is determined by the steps described below. Initially a step of sorting is performed. In this step, one or more of the total contribution values, present in consciousness affect list 870 of FIG. 8G, are arranged in descending order and the identity of the dominant category is established. As explained above, in the consciousness affect list 870 of FIG. 8G, "love" with the highest total contribution value of 53 is the dominant category.

Next, a step of adding predetermined values includes adding the predetermined values for each of the submissions that contributes to the dominant category and arriving at a total of predetermined values. In the example of consciousness affect list 870 of FIG. 8G, two submissions contribute to the dominant category "love" and one of them has a predetermined value of 32 and the other has a predetermined value of 28. Recall these predetermined values were first introduced in grouped lists 840 of FIG. 8D. These two predetermined values are added to arrive at the total of predetermined values of 60.

Then a step of adding submissions is carried out. In this step, the total number of submissions that contribute to the dominant category are added. As mentioned before, in the example of consciousness affect list 870 of FIG. 8G, two submissions contribute to the dominant category "love."

After the above-mentioned steps of adding have concluded, a dividing step is performed. The dividing step includes dividing the total number of predetermined values by the total number of submissions to arrive at a dominant reference value 872 for one or more shares being processed. In the example of consciousness affect list 870 of FIG. 8G, the dividing step provides a dominant reference value of 30 (i.e., 60/2=30).

If the dominant reference value 872 is less than a default intensity value, then the intensity of the dominant category is determined to be "less," and a corresponding visual representation indicates an object of a small size and/or a corresponding audible sound of a lower volume or of a different tone is generated as the or part of the consciousness affect of one or more of the shares.

If the dominant reference value 872 is more than a default intensity value, then the intensity of dominant category is determined to be "more," and a corresponding visual representation indicates an object of a large size and/or a corresponding audible sound of a higher volume or of another different tone is generated as the or part of the consciousness affect of one or more of the shares.

If the dominant reference value 872 is substantially the same as a default intensity value, then the intensity of dominant category is determined to be "default," and a corresponding visual representation indicates an object of a normal size and/or a corresponding audible sound of a normal volume or of a yet another different tone is generated as the or part of the consciousness affect of one or more of the shares.

In the example of consciousness affect list 870 of FIG. 8G, the category of "love" has a dominant reference value 872 of 30, which is equal to the predetermined value of "love" for a default intensity. Thus, in one embodiment, the consciousness affect or part of the consciousness affect of the present invention shows a visual and/or an audible representation of "love" of "default" intensity.

Figures 9A, 9B:
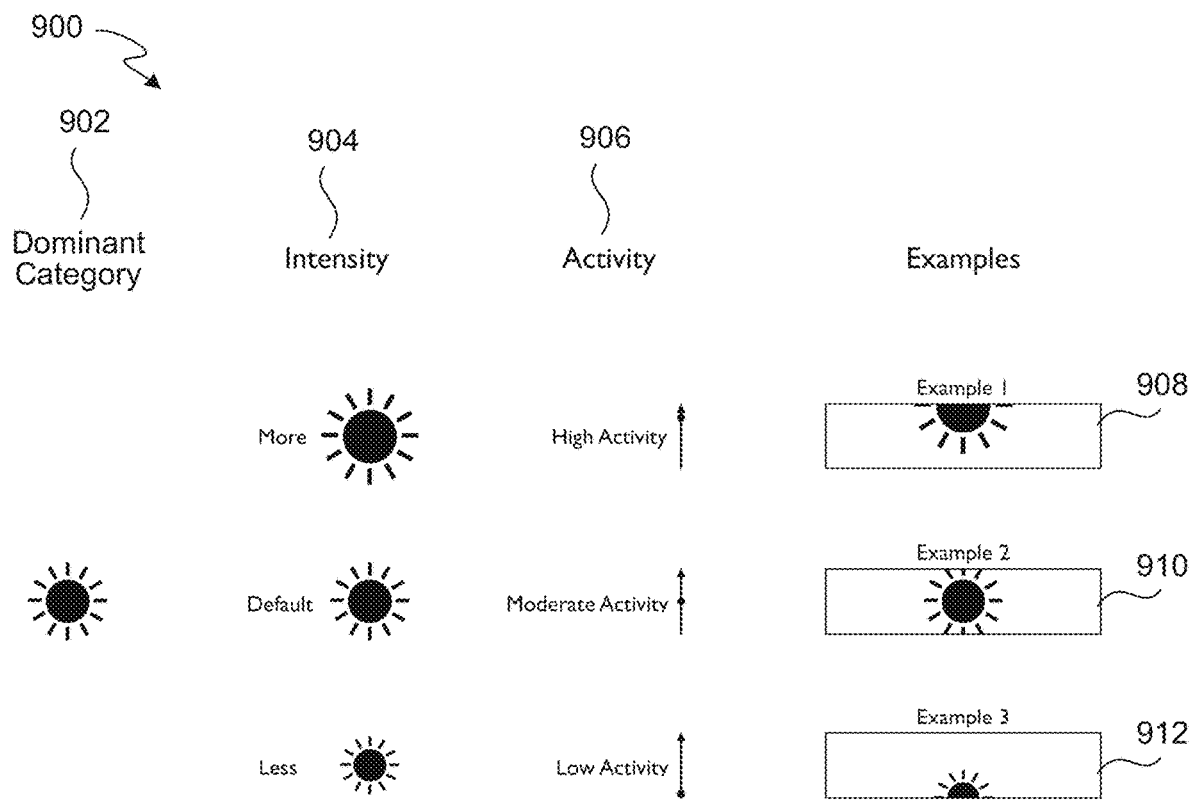
FIG. 9A shows a visual representation, according to one embodiment of the present teachings, for the consciousness affect.
FIG. 9B shows an electronic lookup table, according to one embodiment of the present teachings, for determining a color associated with the consciousness affect and that is displayed on the client device.

FIG. 9A shows various potential aspects of visual representation 900, according to one embodiment of the present teachings, of consciousness affect as it is displayed on a client device. Visual representation 900 identifies the dominant category of "love" 902, as determined in the consciousness affect list 870 of FIG. 8G, with a visual representation of a sun. Further, visual representation 900 identifies intensity 904 (as the intensity of dominant category). To this end, three different exemplar visual representations are provided. A large representation of sun for "more" intensity, a normal representation of sun for "default" intensity and a small representation of sun for "less" intensity are provided.

Further still, visual representation 900 identifies activity 900 to convey the activity index of one or more of the shares. For this aspect of consciousness affect representation, the sun is positioned at an upper portion of the display interface of the client device for high activity, is positioned at middle or center portion of the display interface of the client device for moderate activity, and is positioned at lower portion of the display interface of the client device for low activity. Further still, visual representation 900 identifies all three aspects, i.e., dominant category, intensity and activity index, simultaneously in exemplar display interfaces 908, 910 and 912 of the client device.

In one embodiment of the present teachings, a consciousness affect includes a visual and/or audible representation of consciousness pitch (not shown to simplify illustration in FIG. 9A). A method of determining consciousness pitch begins by initially sorting one or more of the contribution values in descending order. Then, a step of establishing is performed. This step includes establishing the dominant category and the sub-dominant category. By way of example, the consciousness affect list 870 of FIG. 8G, "love" is the dominant category and "hug" is the subdominant category. Next, a subtracting step includes subtracting the sub-dominant category from the dominant category to arrive at a consciousness pitch (hereinafter referred to as the "pitch value") of one or more of the shares being processed for a consciousness affect determination. In the example provided in FIG. 8G, the pitch value is 26 (i.e., 53−27=26).

As with other aspects of consciousness affect, a visual and/or an audible representation of the consciousness affect is conveyed and displayed on the client device. By way of example, each range of pitch values for one or more of the shares is represented by a unique color on the display interface (hereafter also referred to as a "share display color") of the client device. The share display color may be determined, for example, by using an electronic lookup table 920 presented in FIG. 9B. Look up table 920 shows a column 922 for different ranges of pitch values and another column 924 for corresponding different share display colors. According to FIG. 9B, the lookup table shows that for a pitch value of 26 obtained from FIG. 8G, the share display color of "yellow" is displayed on the display interface of the client device.

The integrated visual representation of the various aspects of a consciousness affect (e.g., consciousness affect visual representation 900 of FIG. 9A) of the present teachings provides, among other things, insight into a feeling or mood of one or more users in connection with one or more of the shares that are at issue. By way of example, a patient suffering from a mental disorder is given a new prescription drug. However, the medical staff does not know how the patient will react to the drug. Using the present systems and methods, the patient submits, using a client device, various consciousness inputs and/or shares that the patient believes conveys his/her consciousness state (while under the influence of the drug). The patient's consciousness inputs are processed, according to FIGS. 4A-4I, 5, 6A-6E, 7, 8A-8G, 9A and 9B, to arrive at a consciousness affect with one or more aspects (e.g., at least one of aspect chosen from a group comprising dominant category, intensity of the dominant category, activity index, and consciousness pitch). A visual and/or audible representation of the patient's consciousness affect, on one or more client devices of the medical staff, quickly informs the medical staff of the patient's consciousness state. As a result, the medical staff is in good position to make informed decisions in real time regarding the effectiveness of the drug and/or the health and/or safety of the patient.

The present teachings recognize that humans have relied on their innate biological social feedback system to maintain a high level of understanding while communicating with others. As explained above, the Internet, by its physical-isolating nature, has replaced this social feedback system with a one-button indicator, such as a "Like" or "Heart." In sharp contrast, the present teachings, in one implementation, allow for a visual representation of one or more different aspects of a consciousness affect, which is an accurate representation of this biological social feedback system. The present teachings believe that once its systems and methods are incorporated into electronic communication, users will experience an increased understanding when communicating with others via the Internet and/or electronic devices.

Moreover, the primary objective of advertising, entertainment, and medical are constantly endeavoring to understand the consumers' feelings or mood in connection with products and/or services. According to the present teachings, by relying on a combination of behavioral observations of one or more users afforded by visual and/or audible representation of the consciousness affect, these industries will finally begin to grasp—what consumers' desire, how they think, and what they are feeling.

Figure 10:
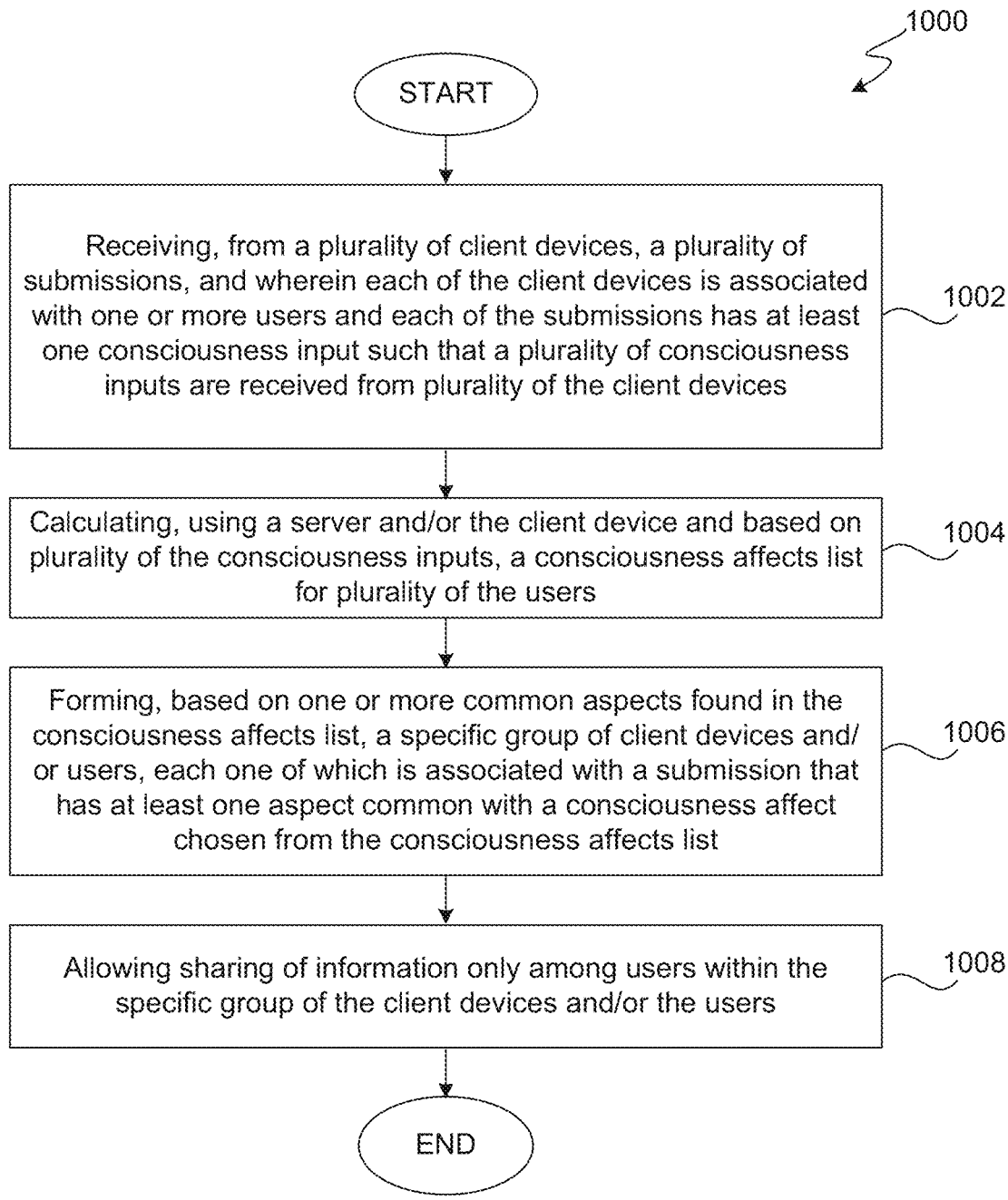
FIG. 10 shows a process flow diagram of a method, according to one embodiment of the present teachings, of forming a group.

The present teachings provide systems and methods forming a group. In one embodiment of the present teachings, FIG. 10 provides a method of forming a group 1000. Method 1000 begins with steps 1002 and 1004, each of which is similar to steps 502 and 504 of FIG. 500, except that steps 1002 and 1004 require receiving submissions from a plurality of devices, which is not necessary for method 500 of FIG. 5. Accordingly, step 1002 includes receiving, from a plurality of client devices, a plurality of submissions. Each of the client devices is associated with one or more users and each submission has at least one consciousness input such that a plurality of consciousness inputs are received from a plurality of the client devices. Step 1004 includes calculating, using a server and/or the client device and based on plurality of the consciousness inputs, a consciousness affects list for plurality of the users.

A step 1006 includes forming, based on one or more common aspects found in the consciousness affects list, a specific group of client devices and/or users, each one of which is associated with a submission that has at least one aspect (e.g., category) common with a consciousness affect chosen from the consciousness affects list. By way of example, users that have consciousness affect that represents "concern" may be joined together as a group.

Step 1008 includes allowing sharing of information only among users within the specific group of client devices and/or users. A user may share information (e.g., location information) with any individual within the specific group of users and/or share information with all users within the specific group. Recall the example of users visiting Yosemite.

More than provide consumer insight, the present teachings allow formation of groups, where the individual members have a common interest, but may not have met each other. This allows doctors and nurses to track patients suffering from a particular ailment and/or experiencing a particular condition. Campaigns may identify and unite their constituents. Purveyor of good and services may similarly identify their target market and effectively engage to advance their brand.

Although illustrative embodiments of this invention have been shown and described, other modifications, changes, and substitutions are intended. Accordingly, it is appropriate that the appended claims be construed broadly and in a manner consistent with the scope of the disclosure, as set forth in the following claims.

What is claimed is:

1. A method of presenting, on a display interface, a visual consciousness affect representation of one or more shares posted on a social media website and/or a social media client device application, said method comprising:
retrieving or receiving, from memory of a client device and/or a server, one or more of said shares posted on said display interface of said social media website and/or said social media client device application presented on one or more client devices, each of said shares contains one or more submissions and an intensity information accompanying each of one or more of said submissions, and wherein said submissions include at least one of icons, text, audio, and/or video;
arriving at, using a client module on said client device and/or a server module on said server, a dominant category of one or more of said shares, said arriving at comprising:
identifying in each of said submissions, information relating to one or more consciousness input types;
extracting, from said information relating to one or more of said consciousness input types, information relating to one or more categories of each of said consciousness input types ("categories") to generate a list identifying one or more extracted categories from each of said submissions;
assigning, based on an age of each of said submissions, a contribution value to each of said submissions and assigning a predetermined value to each of said extracted categories from each of said submissions and wherein said predetermined value assigned to said category at least partially depends on said intensity of said category;
determining, for each of said submissions, a submission's category contribution value, which represents a contribution of each of said submissions to each of said extracted categories present in said list, and wherein said submission's category contribution value equals a product of said contribution value and said predetermined value; and
adding said submission's category contribution value for each of said submissions to arrive at a total contribution value for each said category present in one or more of said shares and wherein said dominant category is said category with a highest total contribution value;
calculating, using said client module on said client device and/or said server module on said server, an intensity of said dominant category of one or more of said shares, said calculating comprising:
sorting one or more of said total contribution values in descending order and establishing one of said extracted categories associated with a highest total contribution value as a dominant category;
adding said predetermined values for each of said submissions that contributes to said dominant category and arriving at a total of predetermined values;
adding number of submissions that contribute to said dominant category and arriving at a total number of submissions;
dividing said total of predetermined values by said total number of submissions to arrive at a dominant reference value;
determining said intensity of said dominant category in one or more shares to be of a calculated value based upon comparison of said dominant reference value with said default intensity value for said dominant category; and
conveying, using said client module and/or said server module, said dominant category of one or more of said shares posted on said social media website and/or said social media client device application and said dominant reference value associated with said dominant category from said client device and/or said server to said social media website and/or said social media client device application presented on a plurality of said client devices;
visually presenting, on said display interface of said plurality of client devices, one or more of said shares and said visual consciousness affect representation corresponding to one or more of said shares, wherein said consciousness affect representation appears adjacent to one or more of said shares, wherein said consciousness affect representation is based on said dominant category of one or more of said shares posted on said social media website and/or said social media client device application, wherein said visual consciousness affect representation is chosen from a group comprising color, weather pattern, image, and animation, and wherein said visual consciousness affect representation is of a predetermined size, such that said predetermined size depends upon said calculated value obtained from said determining said intensity of said dominant category.

2. The method of presenting, on a display interface, a visual consciousness affect representation of one or more shares posted on a social media website and/or a social media client device application of claim 1, wherein said visually presenting includes visually presenting, on said client device, an illustration or photo of an object associated with said category that is identified as being said dominant category.

3. The method of presenting, on a display interface, a visual consciousness affect representation of one or more shares posted on a social media website and/or a social media client device application of claim 1, wherein in absence of retrieving or receiving said intensity information, said predetermined value is assigned a default intensity value.

4. The method of presenting, on a display interface, a visual consciousness affect representation of one or more shares posted on a social media website and/or a social media client device application of claim 1, wherein said determining said intensity of said dominant category provides said calculated value to be any one of a less value, a more value or a normal value, wherein said normal value refers to said dominant reference value that is equal to a default intensity value for said dominant category, wherein said less value refers to said dominant reference value that is less than a default intensity value for said dominant category, and wherein said more value refers to said dominant reference value that is greater than a default intensity value for said dominant category.

5. The method of presenting, on a display interface, a visual consciousness affect representation of one or more shares posted on a social media website and/or a social media client device application of claim 1, wherein in said list is an electronic concatenated list that includes for each of said submissions, an identification of each of said extracted categories, said predetermined value assigned to each of said extracted categories, a timestamp of said submission and an aging index that represents said age of said submission.

6. The method of presenting, on a display interface, a visual consciousness affect representation of one or more shares posted on a social media website and/or a social media client device application of claim 5, further comprising filtering said concatenated list to filter out certain undesired categories and form an electronic filtered list of desired categories.

7. The method of presenting, on a display interface, a visual consciousness affect representation of one or more shares posted on a social media website and/or a social media client device application of claim 6, wherein in said filtering, each of said submissions having a timestamp that is equal to or greater than a threshold timestamp is removed.

8. The method of presenting, on a display interface, a visual consciousness affect representation of one or more shares posted on a social media website and/or a social media client device application of claim 6, further comprising grouping each of said desired categories to form a grouped list, which includes said identification of each of said extracted categories, said predetermined value assigned to each of said extracted categories and said aging index that represents said age of each of said submissions.

9. The method of presenting, on a display interface, a visual consciousness affect representation of one or more shares posted on a social media website and/or a social media client device application of claim 1, further comprising generating a consciousness pitch by subtracting said second highest total contribution value from said highest total contribution value.

10. The method of presenting, on a display interface, a visual consciousness affect representation of one or more shares posted on a social media website and/or a social media client device application of claim 9, further comprising visually presenting, on said client device, said consciousness pitch.

11. The method of presenting, on a display interface, a visual consciousness affect representation of one or more shares posted on a social media website and/or a social media client device application of claim 1, further comprising determining, for each of said shares, an activity index by dividing, for each of said shares, a total number of responses by total number of users involved to arrive at said activity index.

12. The method of presenting, on a display interface, a visual consciousness affect representation of one or more shares posted on a social media website and/or a social media client device application of claim 1, wherein said determining and said calculating are carried out in real-time, which is contemporaneous with said retrieving or said receiving.

13. The method of presenting, on a display interface, a visual consciousness affect representation of one or more shares posted on a social media website and/or a social media client device application of claim 1, wherein in said retrieving or said receiving, one or more of said shares are retrieved or received in an analog and/or a digital state.

* * * * *